US011903533B2

(12) United States Patent
Yoo et al.

(10) Patent No.: US 11,903,533 B2
(45) Date of Patent: Feb. 20, 2024

(54) DRYING APPARATUS AND RELATED METHODS

(71) Applicant: LG ELECTRONICS INC., Seoul (KR)

(72) Inventors: Hyun Sun Yoo, Seoul (KR); Seung Yup Lee, Seoul (KR); Sang Yoon Lee, Seoul (KR); Byung Soo Oh, Seoul (KR); Hyun-Joo Jeon, Seoul (KR); So Ra Cheon, Seoul (KR); Ji Sun Yoon, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 789 days.

(21) Appl. No.: 17/014,595

(22) Filed: Sep. 8, 2020

(65) Prior Publication Data

US 2021/0289999 A1 Sep. 23, 2021

Related U.S. Application Data

(60) Provisional application No. 62/992,138, filed on Mar. 19, 2020.

(30) Foreign Application Priority Data

Apr. 29, 2020 (KR) .......................... 10-2020-0052551

(51) Int. Cl.
*A47K 10/48* (2006.01)
*A61L 9/20* (2006.01)
*A61L 2/00* (2006.01)

(52) U.S. Cl.
CPC ............ *A47K 10/48* (2013.01); *A61L 2/0047* (2013.01); *A61L 9/20* (2013.01); *A61L 2202/11* (2013.01); *A61L 2202/14* (2013.01)

(58) Field of Classification Search
CPC ......... A47K 10/48; A61L 2/0047; A61L 9/20; A61L 2202/11; A61L 2202/14
USPC ............................................................ 34/90
See application file for complete search history.

(56) References Cited

U.S. PATENT DOCUMENTS

| 4,782,601 | A | * | 11/1988 | Gonzalez | ............... | A47K 10/48 |
| | | | | | | 219/217 |
| 5,007,182 | A | * | 4/1991 | Fishman | ................ | A47K 10/48 |
| | | | | | | 34/523 |
| 5,613,304 | A | * | 3/1997 | Lin | ........................ | G01G 19/44 |
| | | | | | | 177/264 |
| 6,705,023 | B1 | * | 3/2004 | Hoover | .................. | A47K 10/48 |
| | | | | | | 392/382 |
| 7,278,225 | B1 | * | 10/2007 | Espinosa | ................ | A47K 10/48 |
| | | | | | | 34/233 |

(Continued)

FOREIGN PATENT DOCUMENTS

EP 3881743 A1 * 9/2021 ............. A47K 10/48
JP 2004538114 A * 12/2004

(Continued)

*Primary Examiner* — Stephen M Gravini
(74) *Attorney, Agent, or Firm* — Bryan Cave Leighton Paisner LLP

(57) ABSTRACT

A drying apparatus includes a body and a rotatable foot pad located on the lower part of the body to dry a user's feet. An air inlet is provided, and a flow generator to receive inlet air from the air inlet and generate an airflow to the top surface of the foot pad.

20 Claims, 48 Drawing Sheets

(56) References Cited

U.S. PATENT DOCUMENTS

| | | | | |
|---|---|---|---|---|
| 8,065,814 B2* | 11/2011 | Olvera | ............... | A47K 10/48 |
| | | | | 34/232 |
| 11,576,539 B2* | 2/2023 | Yoo | ............... | A47K 10/48 |
| 11,596,278 B2* | 3/2023 | Yoo | ............... | A47K 10/48 |
| 2021/0289999 A1* | 9/2021 | Yoo | ............... | A61L 2/0047 |
| 2021/0290006 A1* | 9/2021 | Yoo | ............... | A47K 10/48 |
| 2021/0401127 A1* | 12/2021 | Yoo | ............... | A43D 3/1408 |
| 2022/0061606 A1* | 3/2022 | An | ............... | B01D 46/001 |
| 2023/0212814 A1* | 7/2023 | Kim | ............... | D06F 59/02 |
| | | | | 34/389 |

FOREIGN PATENT DOCUMENTS

| | | | | |
|---|---|---|---|---|
| KR | 2015112340 A | * | 10/2015 | |
| KR | 2022028825 A | * | 3/2022 | |

\* cited by examiner

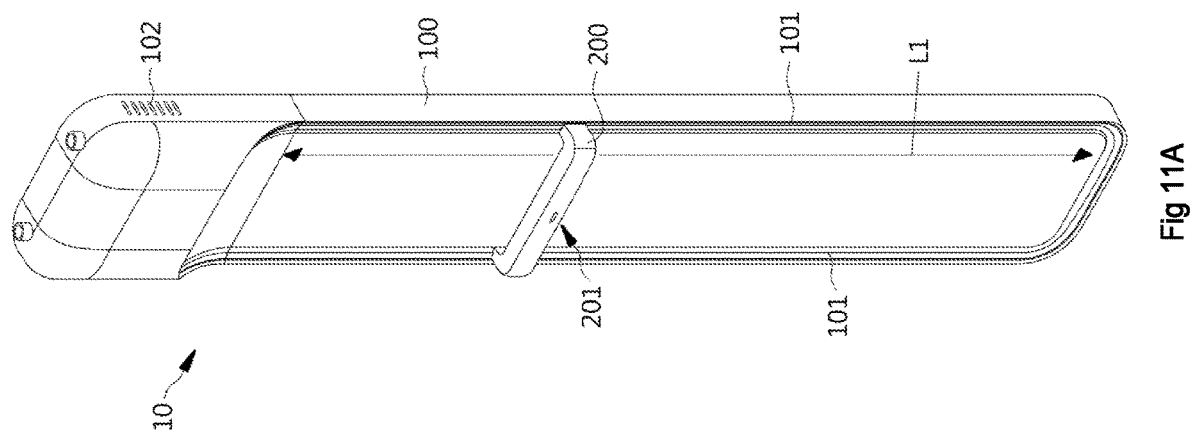

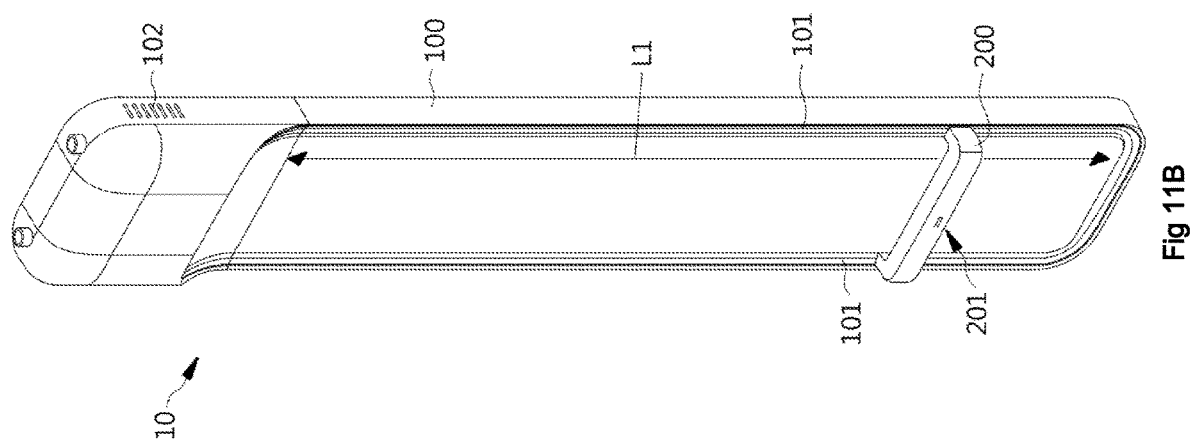

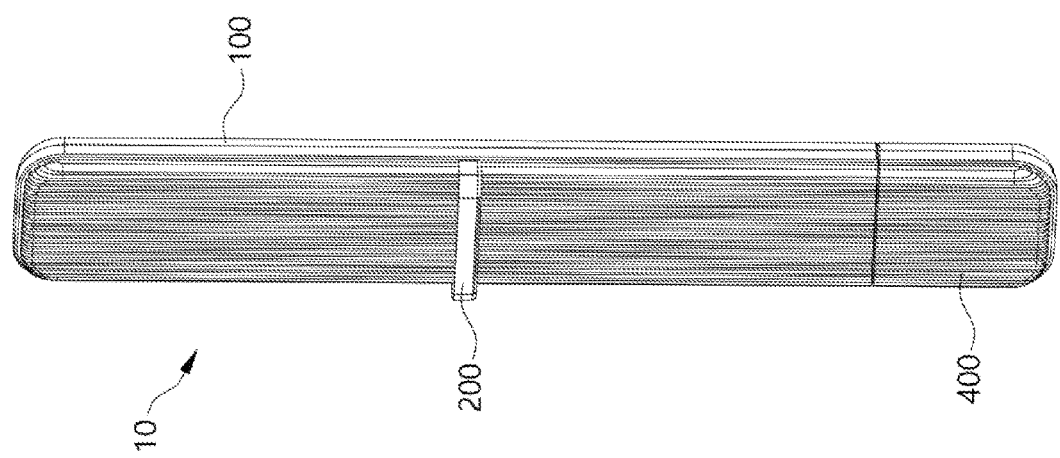

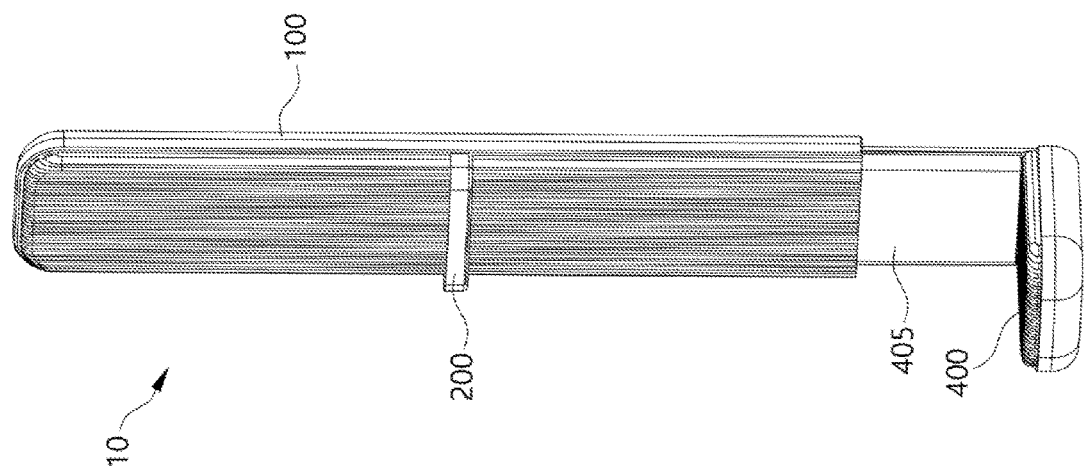

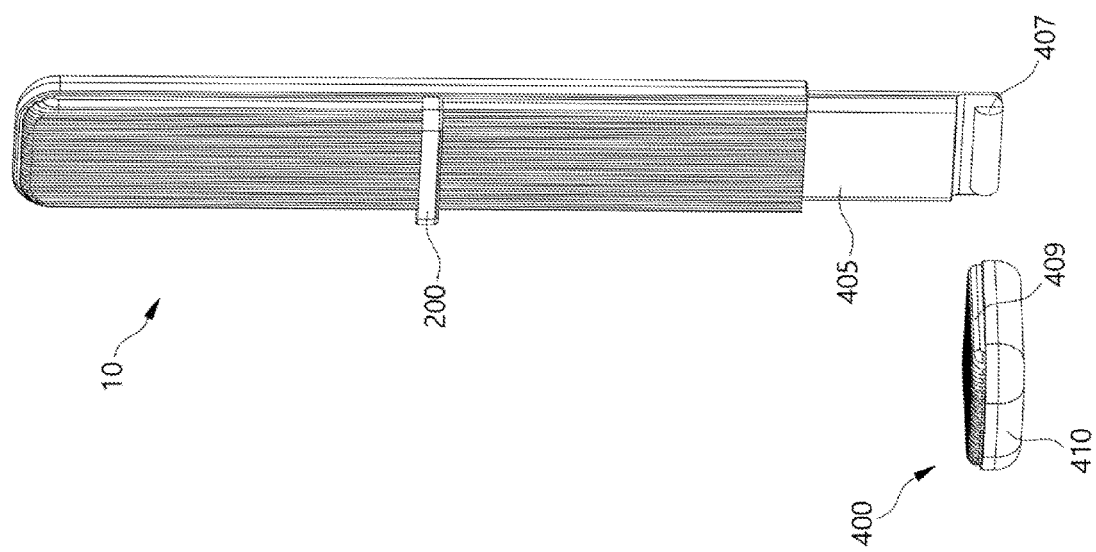

DRYING APPARATUS AND RELATED METHODS

CROSS-REFERENCE TO RELATED APPLICATIONS

This application claims priority to and the benefit of U.S. Provisional Application No. 62/992,138, filed on Mar. 19, 2020 and Korean Patent Application No. 10-2020-0052551, filed on Apr. 29, 2020, the disclosure of which is incorporated herein by reference in its entirety.

FIELD OF THE DISCLOSURE

The present disclosure relates to drying apparatuses and methods of drying, and more particularly, but not solely, to apparatuses for drying of a person or parts of the person.

BACKGROUND

In this specification where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

Regular showering or bathing are commonplace activities across modern society. In many cultures, a shower bath is taken on a daily basis. People may even wash more than once a day, for example, where they have done some form of exercise during the day.

As a result of washing, or also due to perspiration, a person may become wet. Drying of this moisture is important to a person's health in order to prevent bacterial and fungal growth on the person.

Given the right environment, such moisture may evaporate away on its own, but for expediency and comfort, most people towel themselves dry following washing or exercise. Toweling can be a good way to remove water from a person, but drying effectively to prevent bacterial and fungal growth—particularly around the feet—can be time consuming thus such areas may commonly be inadequately dried. Towel drying of hair, particularly for those with long hair, can additionally be a frustrating and involved process.

Aside from any issues with the use of towels to desirably dry a person, the number towels used and frequency of their use means that towels account for a significant proportion of total laundry loads. This is particularly the case in settings where towels are only used once, such as in gyms, sports clubs, and commonly in hotels.

Laundering of towels is energy intensive, and consumption of fresh water is also of concern from an environmental point of view. The depletion of fresh water resources is known to be a widespread issue across many parts of the world. The number of towels washed and frequency with which they are commonly washed consumes significant amounts of water resources.

It is desired to address or ameliorate one or more of the problems discussed above by providing a drying apparatus to at least provide the public with a useful alternative.

While certain aspects of conventional technologies have been discussed to facilitate the disclosure, Applicants in no way disclaim these technical aspects, and it is contemplated that the claimed invention may encompass or include one or more of the conventional technical aspects discussed herein.

SUMMARY

The present disclosure seeks to address one or more of the above-mentioned issues by providing apparatus and methods that improve health and hygiene, as well as have a positive impact on the environment. For instance, the apparatus and methods of the present disclosure provide for the efficient and effective drying of the person, or parts of the person, that diminishes or eliminates reliance upon towels.

It should be understood that, unless expressly stated otherwise, the claimed invention comprehends any and all combinations of the individual features, arrangements and/or steps detailed herein, including but not limited to those features, arrangements and/or steps set forth in the appended claims.

The disclosure describes a drying apparatus that includes a body and a rotatable foot pad located on the lower part of the body to dry a user's feet. An air inlet is provided, and a flow generator to receive inlet air from the air inlet and generate an airflow to the top surface of the foot pad.

As used herein the term "and/or" means "and" or "or", or both.

As used herein "(s)" following a noun means the plural and/or singular forms of the noun.

For the purposes of this specification, the term "plastic" shall be construed to mean a general term for a wide range of synthetic or semisynthetic polymerization products, and includes hydrocarbon-based polymer(s).

For the purpose of this specification, where method steps are described in sequence, the sequence does not necessarily mean that the steps are to be chronologically ordered in that sequence, unless there is no other logical manner of interpreting the sequence, or expressly stated.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

Other aspects of the embodiments of the invention may become apparent from the following description which is given by way of example only and with reference to the accompanying drawings.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

Preferred embodiments or aspects of the invention will be described by way of example only and with reference to the drawings, in which:

FIG. 11A is a perspective view of the drying apparatus of FIG. 1 with a bar thereof in a first position.

FIG. 11B is a perspective view of the drying apparatus of FIG. 1 with the bar thereof in a second position.

FIGS. 33A and 33B are perspective views of a drying apparatus having a foot pad in a stowed condition (FIG. 33A, and a deployed condition (FIG. 33B) according to an embodiment of the present invention.

FIG. 37 is a perspective view of one embodiment as described showing the foot pad detached from the body.

DETAILED DESCRIPTION OF PREFERRED EMBODIMENTS

Reference is made in detail to one or more embodiments of the present invention, examples of which are illustrated in the accompanying drawings.

A drying apparatus may be provided according to the disclosure for a range of applications. In at least a primary application, the drying apparatus may be a dryer for drying a person, such as following bathing or showering. The drying apparatus may be provided as a supplement to towel drying, or in various preferred forms may be provided as a substitute for towel drying. By the use of the drying apparatus as a body dryer, a person may present themselves and be dried by one or more forced airflows of the drying apparatus.

Figure 1:
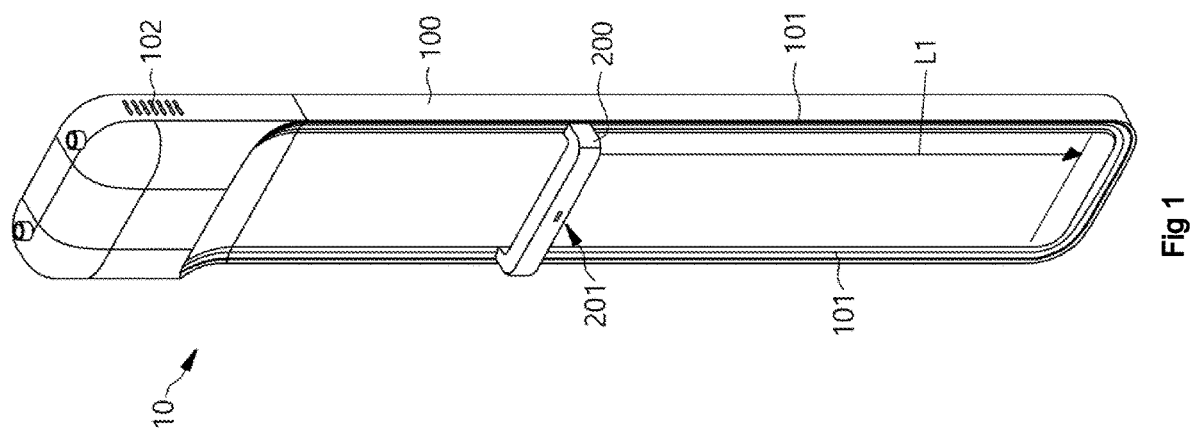
FIG. 1 is a perspective view of a drying apparatus according to an embodiment of the present invention.
Figure 2:
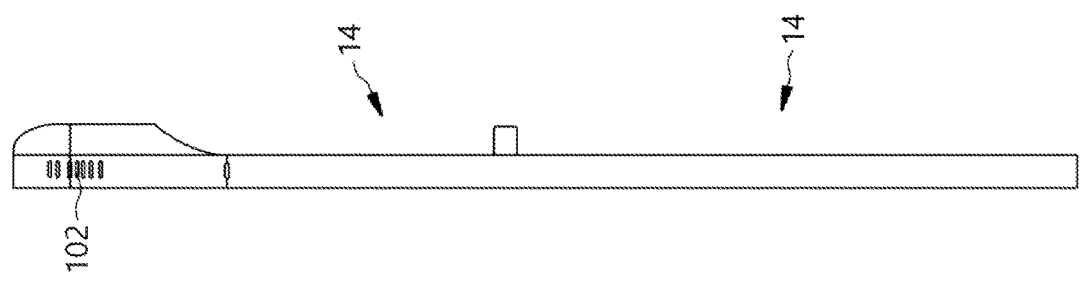
FIG. 2 is a side view of the drying apparatus according to the embodiment of FIG. 1.
Figure 3:
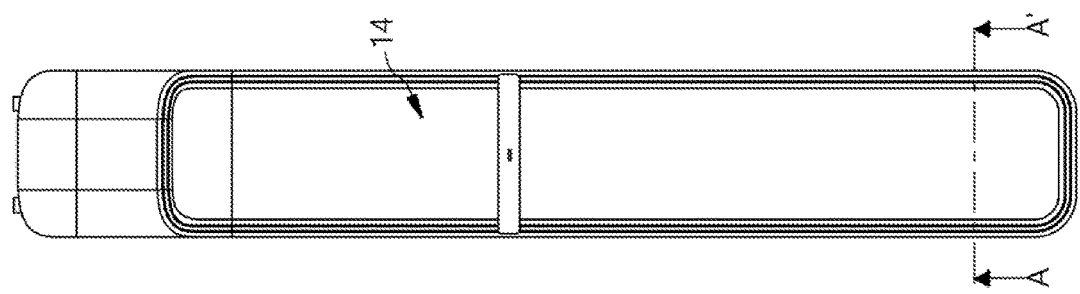
FIG. 3 is a front view of the drying apparatus according to the embodiment of FIG. 1.

FIG. 1 is a perspective view of a drying apparatus according to an embodiment of the present invention; FIG. 2 is a side view of the drying apparatus; and FIG. 3 is a front view of the drying apparatus.

Referring to FIG. 1, a drying apparatus 10 may comprise a body 100 and a bar 200. While the term "bar" is used, "bar" should not be construed as being limited to a bar shape but may have various kinds of shapes according a design criteria or an intended result. The bar 200 may be supported by the body 100, and may be moveable relative to the body 100. The bar 200 may be driven relative to the body 100 by a drive apparatus, as will be explained in greater detail herein.

The drying apparatus 10 may be sized so as to correspond to human body dimensions. For example, in the configuration of the drying apparatus as shown in FIG. 1, the drying apparatus 10, and in particular the body 100, may be sized in proportion to human body dimensions to enable the delivery of the forced airflow across the human body.

The forced airflow may be provided through a first air outlet 101 distributed along a periphery of the body 100. The forced airflow may also be provided through a second air outlet 201 located at the bar 200. Unlike the first air outlet 101 which is stationary with respect to the body 100, the second air outlet 201 moves as the bar 200 travels along a longitudinal length L1 of the body 100 to expel forced airflow to different parts of the human body.

The body 100 may define a drying side or face 14 adjacent to which a user may present themselves for drying by the drying apparatus 10. The drying face 14 may generally define a face or plane from which the forced airflow is provided by the drying apparatus 10 through the first air outlet 101 and/or the second air outlet 201. For example, FIG. 2 shows a side view and FIG. 3 shows a front view of such a drying face 14.

For example, when the drying apparatus 10 is to be provided within a confined space, such as a bathroom, it may be desirable that a minimum of space is taken up by the drying apparatus 10, and perhaps, be aesthetically pleasing. To this end, the portion including the drying face 14 of the body 100 may be provided having a low profile, such as is seen in the side view of FIG. 2. This low profile may provide for a slim look.

To achieve this low profile, at least some internal components of the body 100 which are bulky may be distributed toward an upper region of the body 100 (in the vicinity of the air inlets 102 shown in FIG. 2), so as not to interfere with the low profile of the portion having the drying face 14. The upper region of the body 100 may be at or above the head of a user. The upper region may include the bulky components such as flow generators, thermoelectric devices, flow guides, and the like. In an alternative embodiment, the internal components of the body 100 may be distributed toward a lower region of the body 100 (not shown) providing for an upper region of the body to have a minimized depth.

Figure 4:
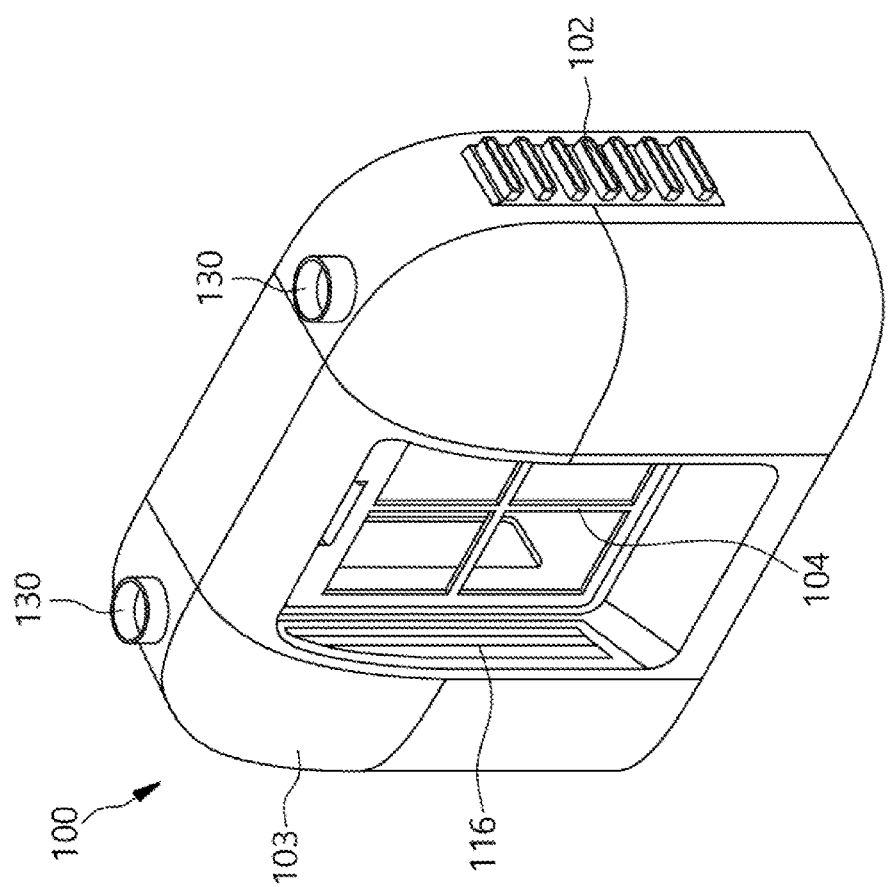
FIG. 4 is a view of an upper region of the drying apparatus according to the embodiment of FIG. 1.
Figure 5:
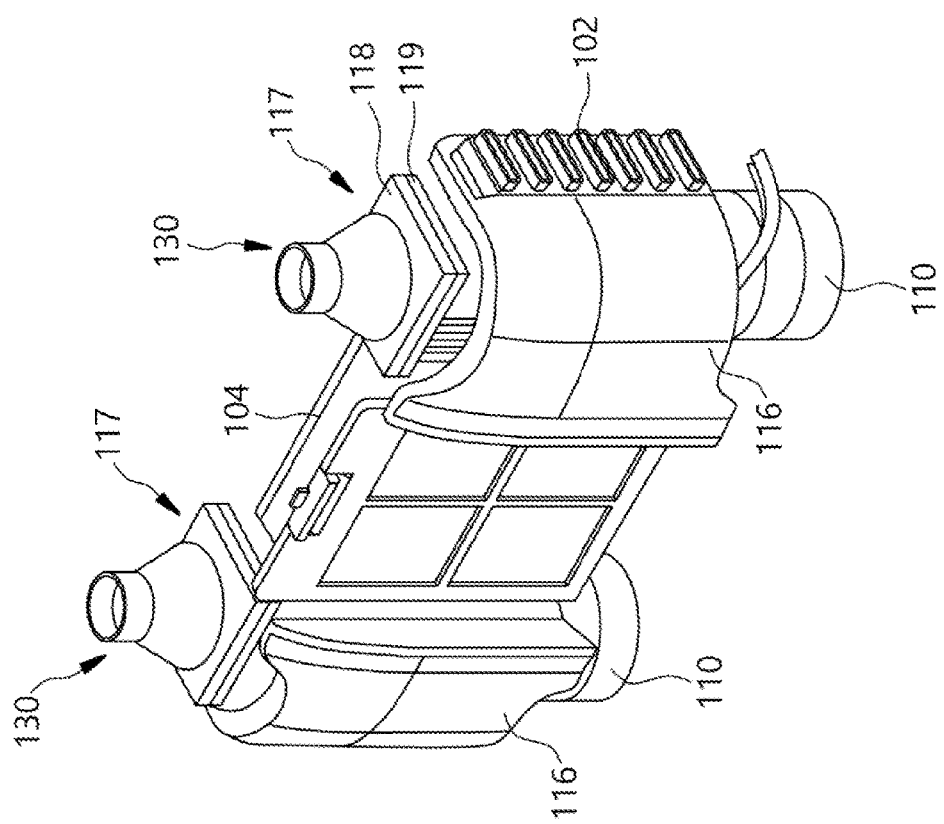
FIG. 5 is a view showing some internal components of the upper region of FIG. 4.

FIG. 4 is a view of details of an example upper region of the body 100. In particular, in FIG. 4 a front cover of the upper region has been removed to expose an outlet of one of two flow guides 116, adjacent to a filter unit 104. The other air flow guide 116 is not visible in FIG. 4, but may be provided on the other side of FIG. 4. The filter unit 104 is in opposition to and/or cooperation with flow guide 116 and arranged in a recess at the center of the body 100. The filter unit 104 may or may not be replaceable. Front cover (not shown in FIG. 4) may be removed to replace an old filter unit 104 with a new filter unit. FIG. 5 shows the coverings of the upper region removed to expose some internal components of the upper region of the body 100 shown in FIG. 4.

Referring to FIGS. 4 and 5, together, the upper region of the body 100 may include a pair of flow generators 110, a pair of flow guides 116, a pair of thermoelectric devices 117 (this device includes, for example, a thermoelectric module, a thermoelectric cooler, or other suitable devices), a pair of air inlets 102, the filter unit 104, and the flow generator housing 103 to house the internal components. While one embodiment uses thermoelectric devices 117 which are devices using thermoelectric effect such as Peltier effect, alternative embodiments may include air conditioning or heat-pump systems using a pump, compressors, and evaporators, resistive heating elements, combustion, or other chemical reaction to control temperature. However, other types of air conditioning devices may be used. In one aspect, the upper region may be considered as an air conditioning system of the body 100.

In the illustrated embodiment, a pair of flow generators 110 are used. In alternative embodiments, only a single flow generator, or a greater number of flow generators, may be used. A flow generator may be an axial fan or the like. Embodiments that include multiple flow generators may cooperate to produce an even airflow into the body 100. Embodiments also include generating independent airflows into the body 100 to vary the strength of the airflow at various portions of the body 100. In the present embodiment, outside air may be received into the flow generator housing 103, by operation of the pair of flow generators 110, through a pair of air inlets 102. The pair of air inlets 102 provide inlet points for outside air into the body 100.

As seen in FIG. 5, each flow generator 110 has its own respective air inlet 102. However, a single inlet 102 may be used with the pair of flow generators 110. Alternatively, more than two air inlets may be used with the pair of flow generators.

Air received at the air inlets 102 is ducted by respective flow guides 116 located between the air inlets 102 and the filter unit 104. In the present embodiment, each flow guide 116 may also in part define an outlet air flow pathway 105 (see FIG. 7) which may be a portion of a flow path where filtered air from the filter unit 104 flows to a respective flow generator 110. Further details of the flow path including the outlet air flow pathway 105 will be described in connection with the description of FIGS. 6 and 7.

Because the present embodiment is described as comprising a pair of flow guides 116, it will be understood that the following description of one flow guide 116 also reflects the other flow guide of the flow guide pair 116. To this end, each flow guide 116 may have a curved form as seen in FIG. 5. One end of each flow guide 116 is connected to a respective air inlet 102, and the other end opens to the upstream side of the filter unit 104. The body of each flow guide 116 includes a curved inner surface and a curved outer surface. The curved inner surface faces the outlet air flow pathway 105 and forms part of the flow path between the downstream side of the filter unit 104 and a respective flow generator 110.

Thus, each flow guide 116 forms a flow path between a respective air inlet 102 and the upstream side of the filter unit 104. Also each flow guide 116 forms, at least in part, a wall of the flow path between the downstream side of the filter unit 104 and a respective flow generator 110. In this configuration, each flow guide 116 may duct air received from a respective air inlet 102 and pass the air to the filter unit 104. Air passed through the filter unit 104 may flow to the outlet air flow pathway 105 where a flow generator 110 may force the air to the first air outlet 101.

In the configuration above, each flow guide 116 may function to separate between the inlet side and outlet side of the filter unit 104. Each flow guide 116 may also function to separate the air received from the air inlet 102 from the filtered air flowing towards the flow generator 110.

In an alternative configuration, the flow guide 116 may not have a dual function of guiding inlet air to the filter unit and guiding filtered air between the filter unit outlet and the flow generator. For example, the air inlets 102, the flow guides 116, the filter unit 104, and the flow generators 110 may be arranged to be linear or sequentially adjacent to each other. Here, each flow guide 116 only ducts the air between the air inlet 102 and the filter unit 104.

A pair of thermoelectric devices 117 may also be included in the upper region of the body 100. Each thermoelectric device 117 may be a semiconductor device that heats and/or cools air, for example, using the Peltier effect. In alternative embodiments, other types of known thermal elements may be employed, such as, a heater, a cooler, or a combination thereof. For example, a refrigeration cycle, having a compressor, evaporator, and condenser, may be utilized to provide cooling and/or heating of air. In another example, a resistance heater may be utilized to provide heating of the air.

In the present embodiment, there is a pair of thermoelectric devices 117. Thus, in the following description of one of the thermoelectric device 117, it will be understood that other thermoelectric device is the same. To this end, each thermoelectric device 117 has a first side 118 and a second side 119. Depending on the direction of current supplied to the thermoelectric device 117, one side may be cooled or heated while the other side is respectively heated or cooled. For example, when the first side (i.e., outward) 118 is cooled, the second side (i.e., inward) 119 is heated. Conversely, when the first side 118 is heated, the second side 119 is cooled.

Each thermoelectric device 117 may heat or cool the air in the outlet air flow pathway 105 (see FIG. 7) that has passed through the filter unit 104. To facilitate this, the second side 119 of the thermoelectric device 117 may be exposed to the outlet air flow pathway 105. Depending on the operation mode of the thermoelectric device 117, the second side 119 may heat or cool the air passing through the outlet air flow pathway 105. The heated or cooled air may then be sucked into a respective flow generator 110.

A processor may control the direction of the current flowing through thermoelectric device 117. For example, a voltage source coupled to the thermoelectric device 117 may be coupled to an analog-to-digital converter (A/D). The A/D converter may be able to generate positive or negative values to control the voltage and therefore the current applied to the thermoelectric device 117. In other embodiments, the A/D converter could have half of its output values corresponding to negative current and half corresponding to positive current.

An exhaust vent 130 may be provided at the upper region of the body 100 when a thermoelectric device 117 is used in the drying apparatus. FIG. 5 shows a pair of exhaust vents 130 associated with the pair of thermoelectric devices 117 that are included in the upper region of the body 100, as illustrated in FIG. 5. Each exhaust vent 130 may be coupled to the first side 118 of a respective one of the thermoelectric devices 117. One or more exhaust vents 130 may be provided at the upper region of the body.

When the thermoelectric device 117 operates as a heater, the cool exhaust air may be vented by a respective exhaust vent 130 to the outside of the drying apparatus 10. When the thermoelectric devices 117 operates as a cooler, the hot exhaust air may be vented by the exhaust vents 130.

Figure 6:
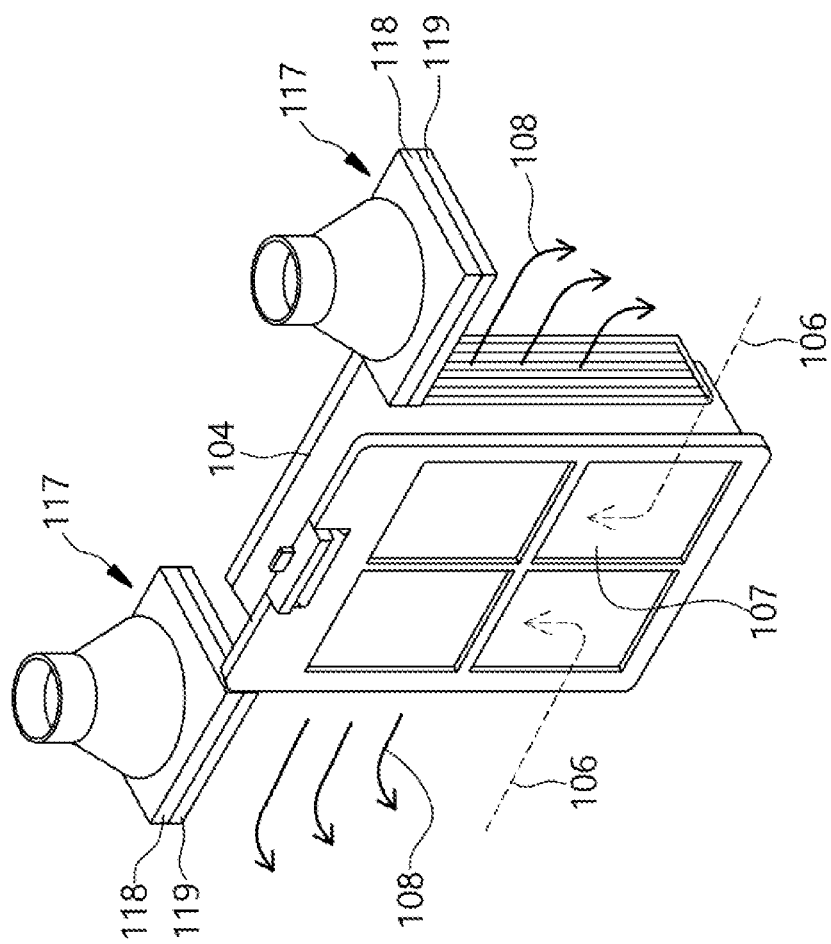
FIG. 6 is a view of an air flow through the internal components of the upper region of FIG. 5.
Figure 7:
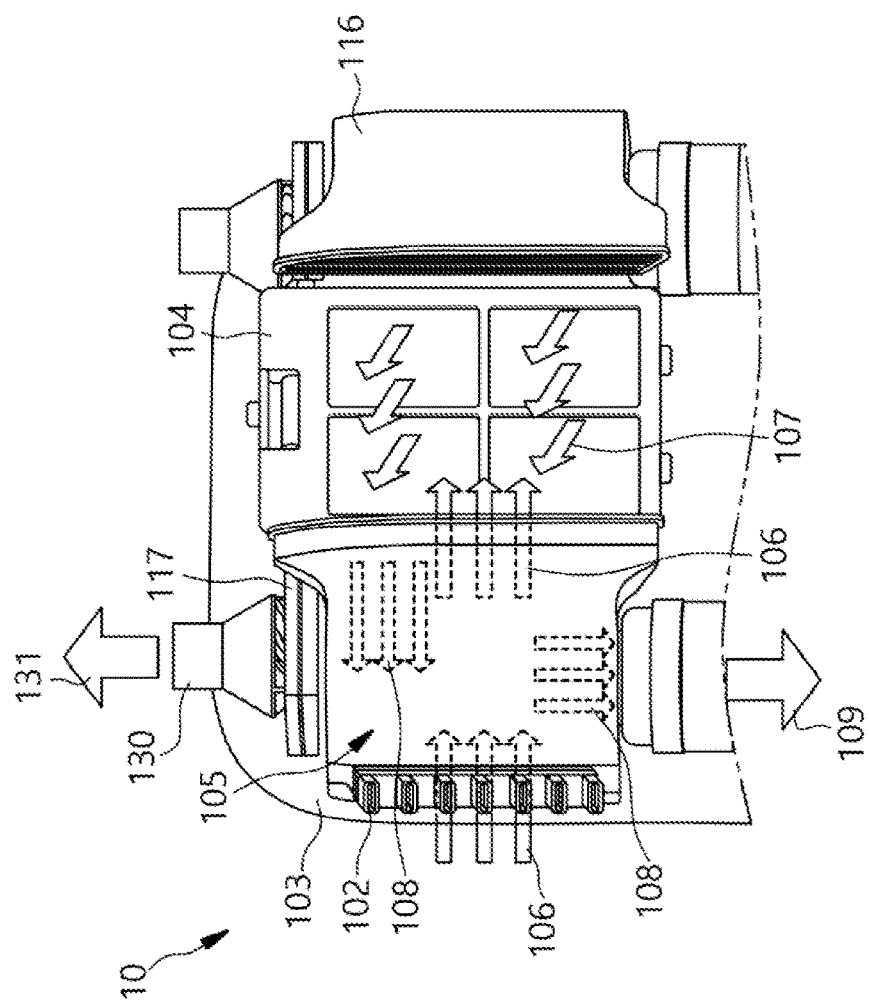
FIG. 7 is another view of the air flow through the internal components of the upper region.

FIG. 6 is an illustration of air flow through the parts of the upper region of the body 100 according to the embodiment of the present invention. FIG. 7 is another illustration of the air flow through the parts of the upper region of the body 100. The air flow through the components of the upper region of the body 100 will be described with respect to one flow generator 110 as the air flow will be similar for the other flow generator 110.

The present embodiment will now be described in greater detail with reference to FIGS. 6 and 7. When the flow generator 110 operates, air is received through the air inlet 102 and through the flow guide 116 thereby arriving at the front surface of the filter unit 104 as illustrated by air flow arrows 106 and 107 in FIG. 7. The air then passes through the front surface of the filter unit 104. The filtered air exits through the sides of the filter unit 104.

The filtered air, after exiting filter unit 104, arrives at the outlet air flow pathway 105 illustrated by air flow arrows 108 in FIG. 7. The filtered air in the outlet air flow pathway 105 may be heated or cooled by the thermoelectric device 117. The exhaust air from the thermoelectric device 117 may then be vented by the exhaust vent 130 as described above, and as illustrated by air flow arrow 131. The heated or cooled air illustrated by air flow arrow 108 is sucked down into and through the flow generator 110, and then forced, by the flow generator 110, onwards to the first air outlet 101, as illustrated by air flow arrow 109 in FIG. 7.

A configuration of an air conditioning system of the body 100 has been described above. The drying apparatus 10 having the configuration above may vent cool air or hot air to condition a space in which the drying apparatus is occupying. The space may be a bathroom. During hot days the drying apparatus 10 may cool the bathroom. During cold days the drying apparatus 10 may heat the bathroom. The drying apparatus may also use the air conditioning system described herein to dry a user. For example, the cool air or hot air forced by the flow generator 110 is vented by the first air outlet 101 along the periphery of the body 100 at the drying face 14 (see FIGS. 1-3). A user presenting themselves at the drying face 14 may dry themselves through the vented cool air or hot air.

Figure 8:
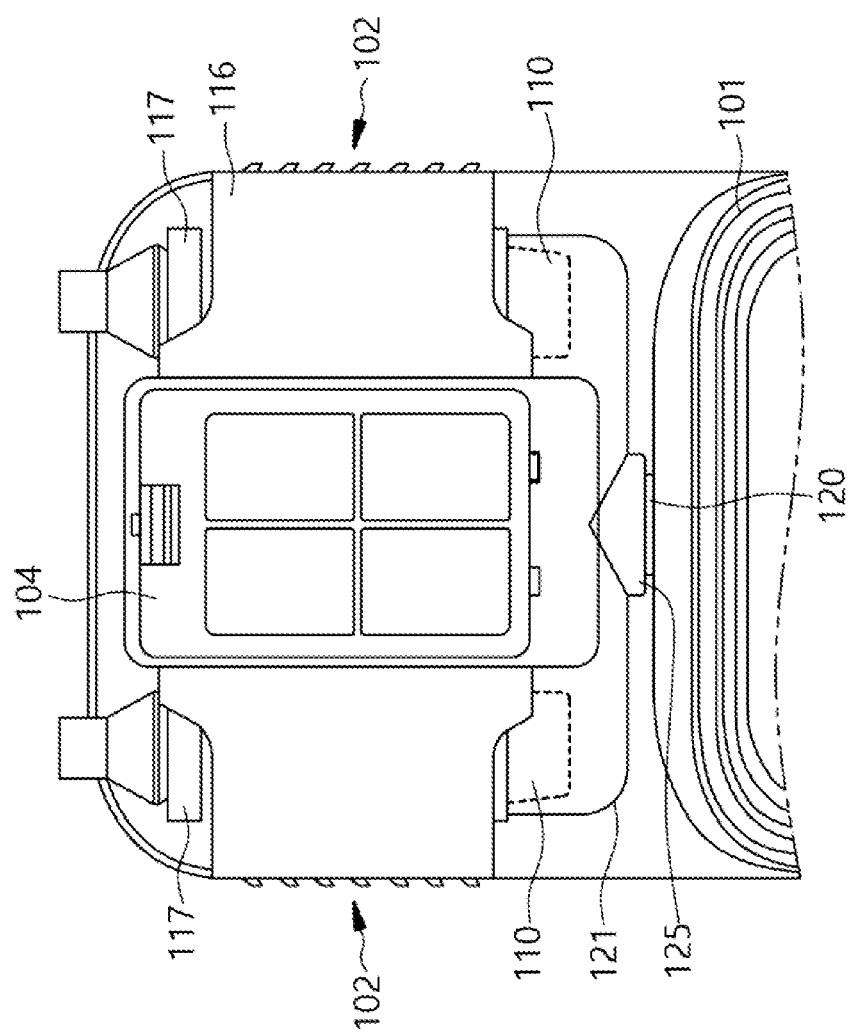
FIG. 8 is a view showing a connection between flow generators and a first air outlet according to an embodiment of the present invention.

FIG. 8 is a view illustrating a connection between the flow generators 110 and the first air outlet 101 of the body 100, according to an embodiment of the present invention.

As shown, the flow generators 110 force the airflow into a duct 121. At the duct 121, the forced airflows from the two flow generators 110 are combined into a single forced airflow. The duct 121 then guides the combined forced airflow through a common opening 125 into the first air outlet 101 of the body 100. In the present embodiment, a resistance heater 120 is disposed at the common opening 125 to further heat the forced airflow. This configuration may be used where it is desirable that a heated forced airflow from the flow generators 110 is further heated prior to being expelled into the first air outlet 101. This configuration may be used, for example, where a quick heating of a bathroom is desired or a more heated forced airflow is desired during a drying of the user.

While in FIG. 8, a resistance heater has been illustrated, any other suitable thermal elements may be used. In other configurations the thermal element may be a thermoelectric device that may be used to selectively heat or cool the forced airflow flowing out of the common opening 125.

Figure 9A:
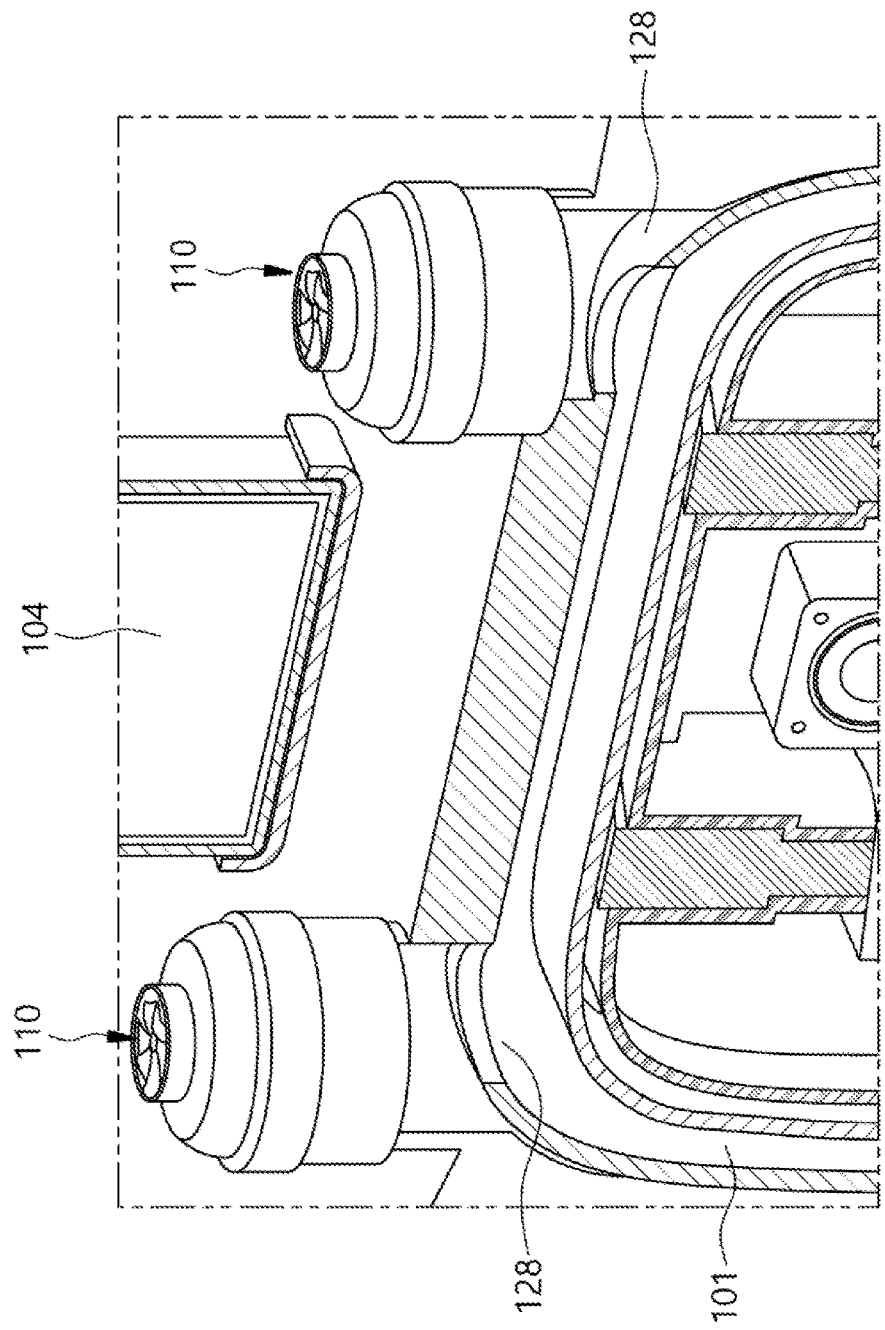
FIG. 9A is a view showing a connection between the flow generators and the first air outlet according to another embodiment of the present invention.

FIG. 9A illustrates a connection between the flow generators 110 and the first air outlet 101 of the body 100 according to an alternative embodiment of the present invention. Unlike the embodiment illustrated in FIG. 8, the outlet of each of the flow generators 110 directly connects to the first air outlet 101 of the body 100 according to the alternative embodiment of FIG. 9A. The first air outlet 101 thus includes air openings 128 at the upper side of the first air outlet 101. Each air opening 128 communicates directly with the outlet of respective one of the flow generators 110. By having the outlet of each flow generator 110 directly connect to the first air outlet 101 of the body 100, the connection structure may be simplified and the forced airflow may be directly expelled into the first air outlet 101.

The forced airflow in the present embodiment may be stronger than the forced airflow of the embodiment of FIG. 8. The reason is that, in the forced airflow of FIG. 8, the vertical direction of the forced airflows of the respective flow generators are forced into a horizontal direction by the duct 121, then made to collide with each other to form a single forced airflow. The duct 121 then forces the single combined forced airflow to flow vertically downward into the first air outlet 101. In contrast, in the embodiment of FIG. 9A, the forced airflows of the respective flow generators flow vertically downward directly into the first air outlet 101.

Figure 9B:
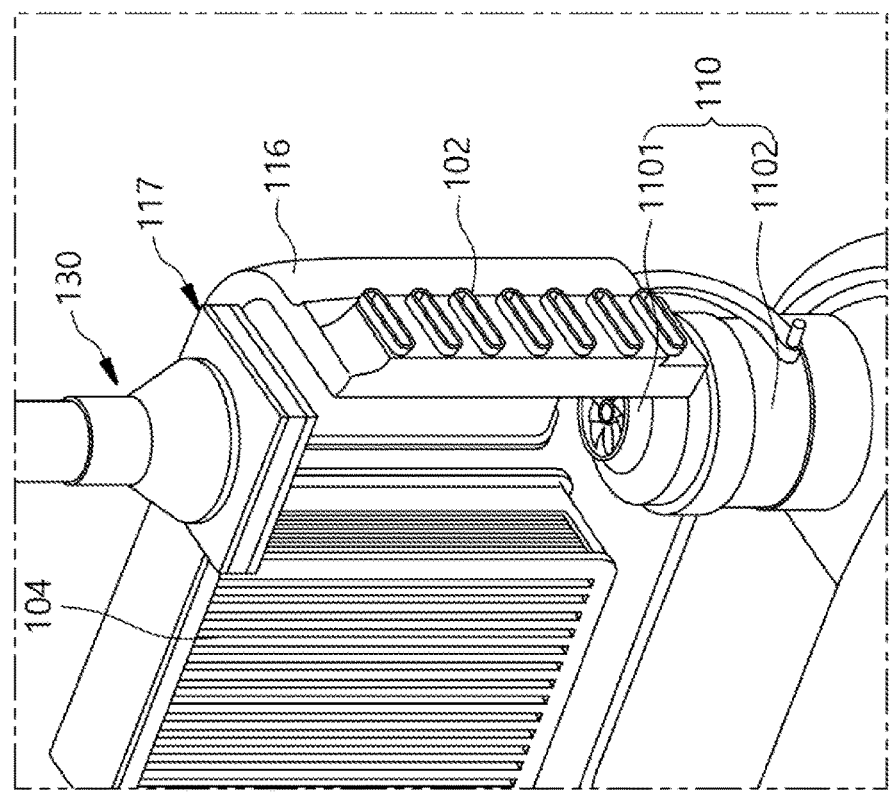
FIG. 9B is a rear perspective view showing a connection between one of the flow generators and the first air outlet of FIG. 9A.

FIG. 9B is a rear perspective view showing a connection between one of the flow generators and the first air outlet of FIG. 9A. As shown in FIG. 9B, in this configuration, the flow generator 110 includes a fan assembly 1101 and a conduit 1102. The fan assembly may be an axial fan and the like. Preferably, the fan assembly includes a high speed motor that sucks in air and expels air at high speed. For example, the fan assembly may be Smart Inverter Motor™ available from LG Electronics, Inc., Republic of Korea, that operates at speeds up to 115,000 revolutions per minute (RPM). Similar fan assembly may be used.

The fan assembly 1101 is connected to the conduit 1102 which may be a cylindrical tube that connects to the first air outlet 101. However, it should be appreciated that the conduit 1102 is not limited to a cylindrical tube and other configurations may be used such as an oval tube, a square tube, a rectangular tube, etc. The conduit 1102 contains the air sucked in by the fan assembly 1101 within the confines of the conduit 1102 thereby increasing the speed of the forced airflow if not maintaining the speed of the forced airflow expelled by the fan assembly 1101. Thus, a forced airflow of relatively high speed is introduced into the first air outlet 101.

Figure 10:
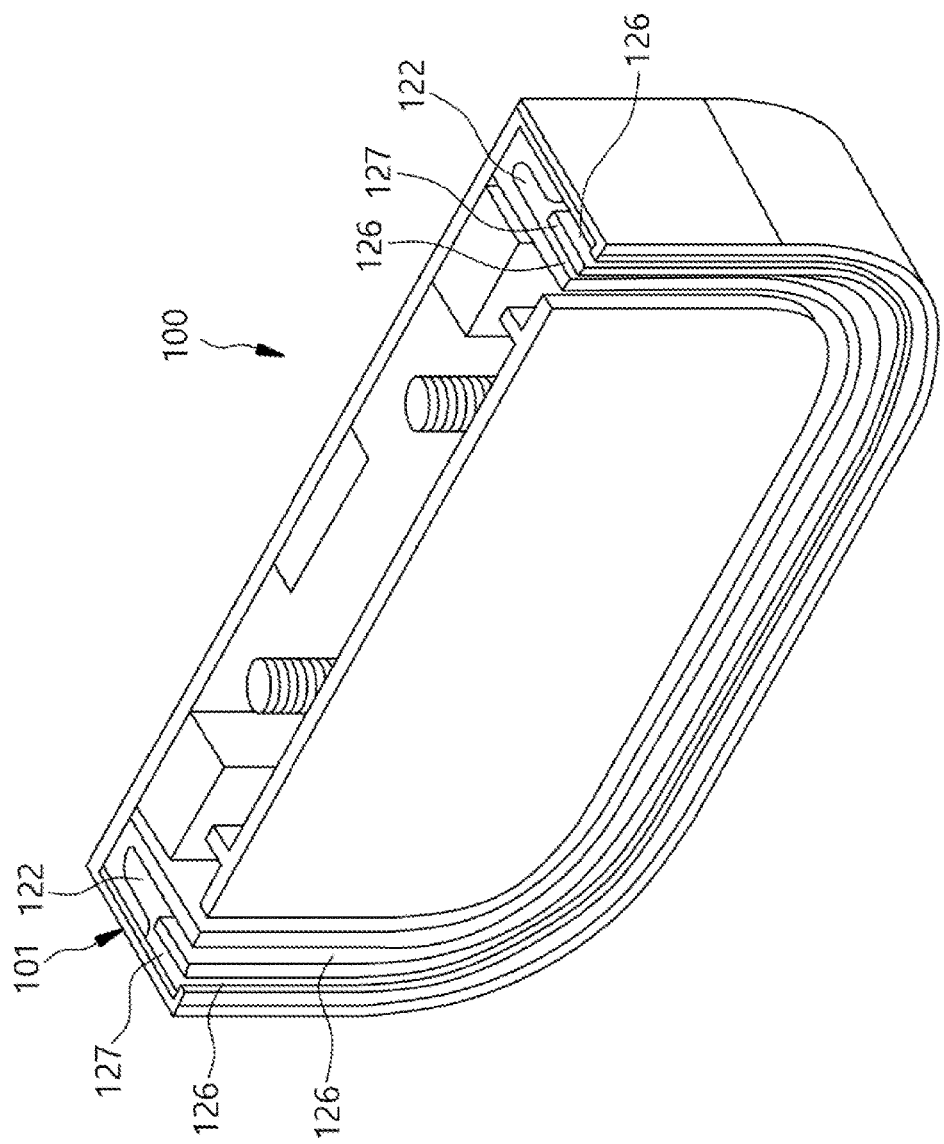
FIG. 10 is a cross-sectional view of the first air outlet along line A-A' of FIG. 3.

FIG. 10 is a cross-sectional view along line A-A' of FIG. 3 further illustrating the first air outlet 101 of the body according to an embodiment of the present invention. As shown in part, the first air outlet 101 is distributed around at least a partial periphery of the body 100. In the present embodiment, the first air outlet 101 actually follows the contour of the periphery of the drying face 14 of the body 100 (see FIG. 3). However, one skilled in the art will readily appreciate that the air outlet 101 could take on any one of a number of other configurations. For example, in an alternative embodiment, the first air outlet 101 may be configured as a plurality of slits placed vertically and/or horizontally across the drying face 14 (see, for example, FIG. 31).

Again, referring to FIG. 10, the first air outlet 101 according to the present embodiment, includes a duct 122, a vent 126, and a fin 127. The duct 122 receives the forced airflow from the upper region of the body 100, and ducts the forced airflow along the periphery of the body 100.

The duct 122 is connected to the vent 126 which also runs along the periphery of the body 100 and is visible from the drying face 14 of the body 100 (see FIGS. 1 and 3). The forced airflow exits the body 100 through the vent 126. The fin 127 may be disposed in the vent 126 which also runs along the periphery of the body 100 and divides the space formed by the vent 126 into two. The fin 127 may aid in directing the forced airflow flowing out from the vent 126. In the present embodiment, the fin 127 is fixed in the vent 126 and directs the forced airflow in one direction which is straight outwardly.

In an alternative configuration, the fin may be adjustable to be moved to the left or to the right to direct the forced airflow exiting the body 100 in the left direction or the right direction, as desired. For example, the fin of the left side of the body 100 may be moved in the right direction and the fin on the right side of the body 100 may be moved in the left direction so that at least a portion of the forced airflow may converge inwardly towards a center with respect to the body 100. Conversely, the fin of the left side of the body 100 may be moved in the left direction and the fin on the right side of the body 100 may be moved in the right direction so that at least a portion of the forced airflow may diverge outwardly away from the center with respect to the body 100.

Thus far, the body 100 of the drying apparatus 10 according to embodiments of the present invention has been described. The drying apparatus 10 may include a bar 200 that may expel forced airflow. The bar 200 may be movable relative to the body 100, as previously mentioned.

FIGS. 11A and 11B are views illustrating a bar 200 at two respective driven positions along the longitudinal length L1 of the body 100 according to the embodiment of the present invention.

The bar 200 may be moveable along the longitudinal length L1 of the body 100 driven by a drive apparatus to be described later. The travel bounds of the bar 200 may be fixed to coincide with longitudinal length L1, of the body 100 or, alternatively, it could be adjustable to more closely coincide with the height by a particular user. Accordingly, the drying apparatus 10 may be configured such that when the user is positioned adjacent to the drying face 14, the desired length (e.g., the height) of the user may be covered by the drying airflow of the second air outlet 201 by the movement of the bar 200. For example, the bar 200 may move from the top position as shown in FIG. 11A to the bottom position as shown in FIG. 11B (and back in repetition if desired) while expelling forced airflow from the second air outlet 201, where the distance traveled between the position of the bar 200 in FIG. 11A and in FIG. 11B may correspond with the height of the user.

Figure 12A:
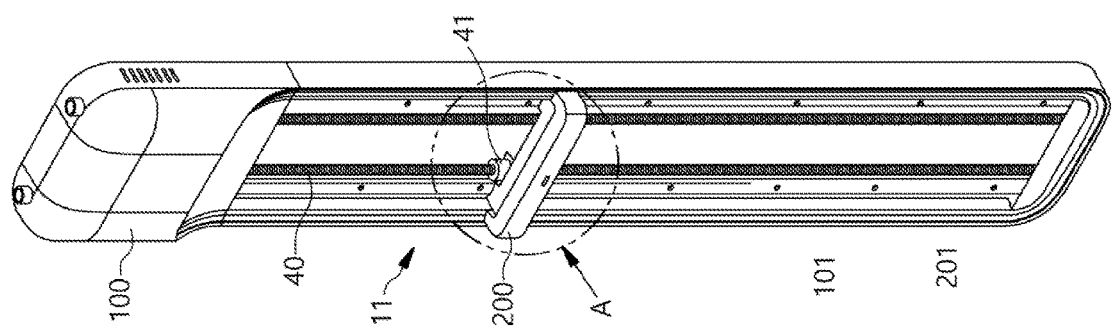
FIG. 12A is a perspective view showing a driving apparatus for a drying apparatus according to an embodiment of the present invention.
Figure 12B:
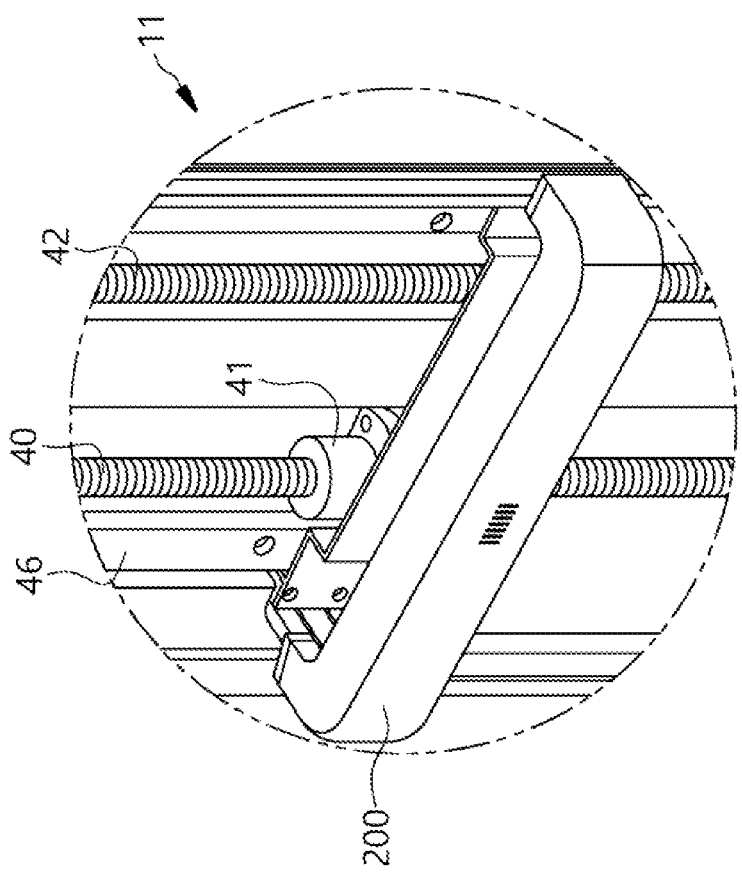
FIG. 12B is a close up view of the portion A of FIG. 12A.
Figure 12C:
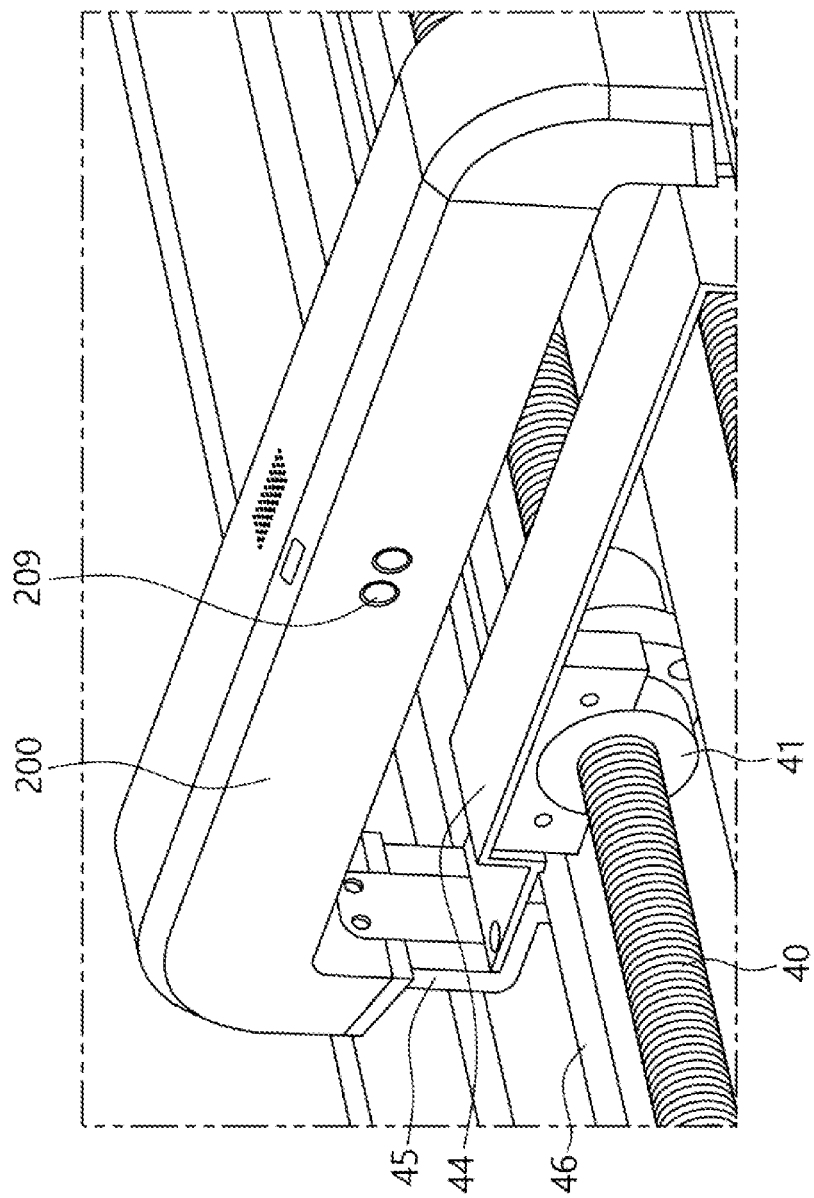
FIG. 12C is bottom view of FIG. 12B.
Figure 12D:
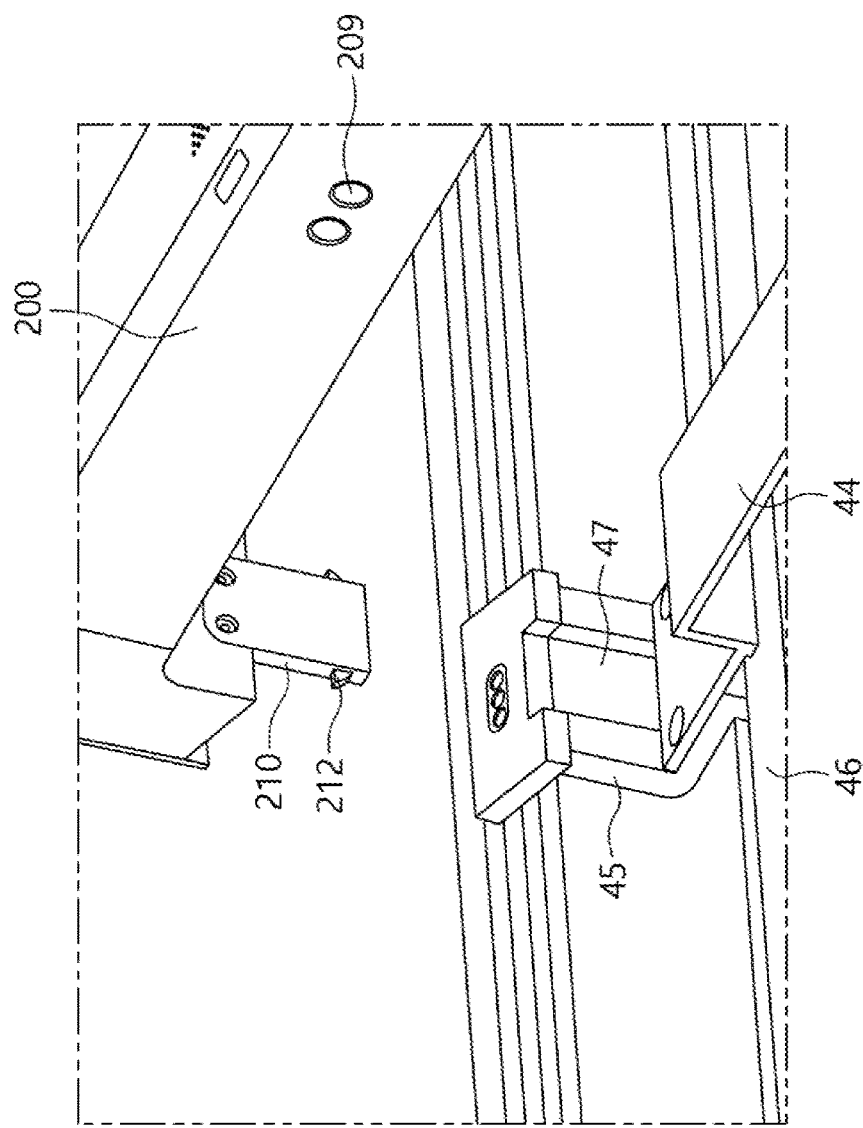
FIG. 12D is a view showing a fastening mechanism of a bar of a drying apparatus according to an embodiment of the present invention.

FIG. 12A is a view illustrating a driving apparatus of the bar 200 according to the embodiment of the present invention. FIG. 12B is a close up view of the drive apparatus illustrated in portion A of FIG. 12A. FIG. 12C is bottom view of the drive apparatus illustrated in FIG. 12B, and FIG. 12D is a view illustrating an exemplary fastening mechanism 210 of the bar 200 according to an embodiment of the present invention.

Referring to FIGS. 12A and 12B, the drive apparatus 11 drives the bar 200 relative to the body 100. The drive apparatus 11 may be provided at the body 100. In accordance with this exemplary embodiment, the drive apparatus 11 includes a lead screw 40, a nut 41, and a motor 50 (see FIG. 13). The lead screw 40 is threaded and may have a length corresponding to the longitudinal length L1 of the drying face 14 of the body 100. The motor 50 may be located at the upper region of the body 100. However, the motor 50 may be located anywhere as long as the motor 50 is able to rotate the lead screw 40 thus causing the nut 41 to move up or down the lead screw 40, depending on the direction of rotation of the lead screw 40, along the longitudinal length L1 of the drying face 14 of the body 100. A shaft of the motor 50 may be coupled to one end of the lead screw 40 (e.g., the upper end of the lead screw 40). Therefore, when the motor 50 rotates the shaft clockwise, the lead screw 40 rotates clockwise. When the motor 50 rotates the shaft counterclockwise the lead screw 40 rotates counterclockwise.

Referring to FIGS. 12B and 12C, the nut 41 is threaded corresponding to the thread of the lead screw 40 and is thus mated with the lead screw 40. The nut 41 is fixed to the bar 200. In the present embodiment, the nut 41 is fixed to a bracket assembly 44 to which the bar 200 is attached. However, one skilled in the art will appreciate that other configurations for fixing the nut 41 to the bar 200, direct or indirect, are possible. When the lead screw 40 is rotated by the motor 50, the nut 41 rides up or down on the lead screw 40 which, in turn, moves the bar 200 up or down.

For example, when the motor 50 rotates the lead screw 40 clockwise, the nut 41 moves up the lead screw 40, which in turn moves the bar 200 up with respect to and along the longitudinal length of the body 100. On the other hand, when the motor 50 rotates the lead screw 40 counterclockwise, the nut 41 moves down the lead screw 40, which in turn moves the bar 200 down with respect to and along the longitudinal length of the bar 200.

In another example, when the motor 50 rotates the lead screw 40 clockwise, the nut 41 moves down the lead screw 40, which in turn moves the bar 200 down with respect to and along the longitudinal length of the body 100. When the motor rotates the lead screw 40 counterclockwise, the nut 41 moves up the lead screw 40, which in turn moves the bar 200 up with respect to and along the longitudinal length of the bar 200.

Figure 13:
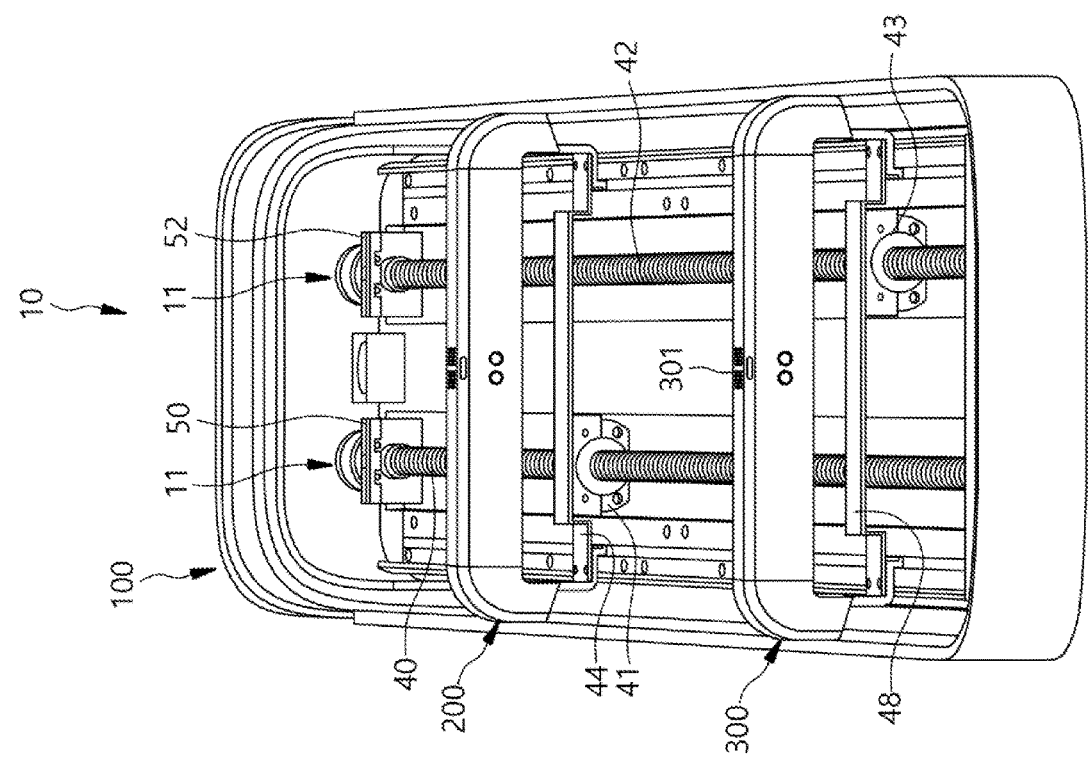
FIG. 13 is a perspective view showing a drying apparatus including additional bars according to an embodiment of the present invention.

Referring to FIGS. 12C and 12D, the bracket assembly 44 may have one or more guide members 45 for running in one or more corresponding guide tracks 46 of the body 100. In the present embodiment, as illustrated in FIG. 13, a dual guide track is used, including a guide track 46 which runs vertically on both sides of the body 100. Together, the guide members 45 and guide tracks 46 guide the bar 200 along a predetermined vertical path.

For example, the guide members 45 and guide tracks 46 may operate to retain the bar 200 against rotational movement about the longitudinal axis which may be caused due to the rotation of the lead screw 40. The dual guide tracks 46 may also provide stability to the bar 200 as it moves up and down along the body 100.

In the present embodiment, the bar 200 may include a fastening mechanism 210 to fasten to the guide member 45 of the bracket assembly 44. A fastening mechanism 210 is provided at both ends of the bar 200 in the present embodiment. The guide member 45 may include a recess 47 having a shape corresponding to the shape of the fastening mechanism 210. When the bar 200 is attached to the bracket assembly 44, the fastening mechanism 210 slides into the recess 47 of the guide member 45, thus attaching the fastening mechanism 210 to the guide member 45.

The fastening mechanism 210 may include one or more protrusions 212 that protrude from the sides of the fastening mechanism 210. The one or more protrusions 212 may be elastically deformable or may be spring loaded. When the fastening mechanism 210 has been fully inserted into the recess 47 of the guide member 45, the one or more protrusions 212 may hook into one or more corresponding slots in the recess 47 to attach the bar 200 to the bracket assembly 44.

The fastening mechanism 210 may provide for easy detachment of the bar 200 from the bracket assembly 44. Because the protrusions 212 are elastically deformable or spring loaded, the bar 200 may be detachable from the body 100 by exerting sufficient force. The bar 200 may be replaced with another bar 200 or may be serviced without the need for taking the entire drying apparatus 10 for servicing.

An embodiment of a drive apparatus using a lead screw and nut has been described. In other exemplary configurations, the bar 200 may be driven upon the body 100 by components other than a lead screw and nut. In fact, any suitable drive apparatus capable of providing the desired relative motion may be used. For example, the lead screw and nut may be replaced by a rack and pinion system, a pulley and belt drive, or, where the desired motion is a linear motion, a linear actuator.

FIG. 13 is a front view showing a drying apparatus including a bar 200 and a second bar 300 according to another embodiment of the present invention.

Referring to FIG. 13, a drying apparatus 10 may comprise a bar 200 and a second bar 300. The second bar 300 may include a third air outlet 301 and may be moveably driven relative the body 100. The second bar 300 may be associated with its own nut 43, and the nut 43 with its own lead screw 42. The nut 43 is fixed to its own bracket assembly 48 such that the second bar 300 may be driven relative the body 100. The lead screw 42 may be driven by its own motor 52. The components associated with the driving of the second bar 300, and the functionality thereof, are similar to that described above with respect to the bar 200, and thus further description will be omitted in order to avoid duplicate description.

Based on the configuration of the exemplary embodiment described above, those skilled in the art will readily appreciate that even more bars may be employed in the drying apparatus 10. The drive apparatus 11 may be modular to accommodate multiple bars at the body 100.

As an example, as shown in FIG. 13, the bar 200 is associated with its own motor 50, lead screw 40, nut 41, and bracket assembly 44. By operation of the motor 50, the lead screw 40, and the nut 41, the bar 200 moves up and down relative to the body 100. Similarly, the second bar 300 is associated with its own motor 52, lead screw 42, nut 43, and bracket assembly 48. By operation of the motor 52, the lead screw 42, and the nut 43, the second bar 300 moves up and down relative to the body 100. The motor, the lead screw, the nut, and the bracket assembly associated with one bar do not act on the other bar. That is, the motor, the lead screw, the nut, and the bracket assembly of one bar only operate on that bar.

Accordingly, with each additional bar, a corresponding motor, a lead screw, a nut, and a bracket assembly may be added to the drive apparatus 11 to accommodate that bar. In this manner the drying apparatus 10 may be configured with a number of bars on the body 100 according to the preference of the user. Alternatively, each drive apparatus may accommodate more than one bar spaced apart from each other, which move in unison along the longitudinal length of the body 100.

FIG. 13 shows the bar 200 and the second bar 300 using the same guide track(s). In alternative exemplary configurations, the bar 200 and the second bar 300 may use separate guide tracks. By this configuration the bar 200 or the second bar 300 may be operated to any desired location along the extent of its drive path, irrespective of the position of the bar 200 or the second bar 300.

Figure 14:
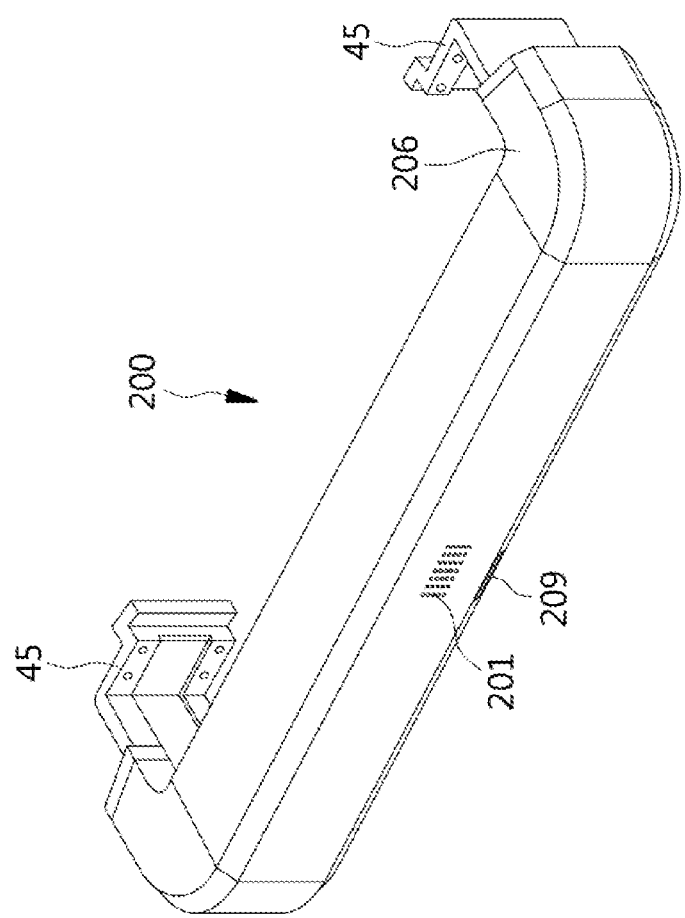
FIG. 14 is a top perspective view of a bar of a drying apparatus according to an embodiment of the present invention.
Figure 15:
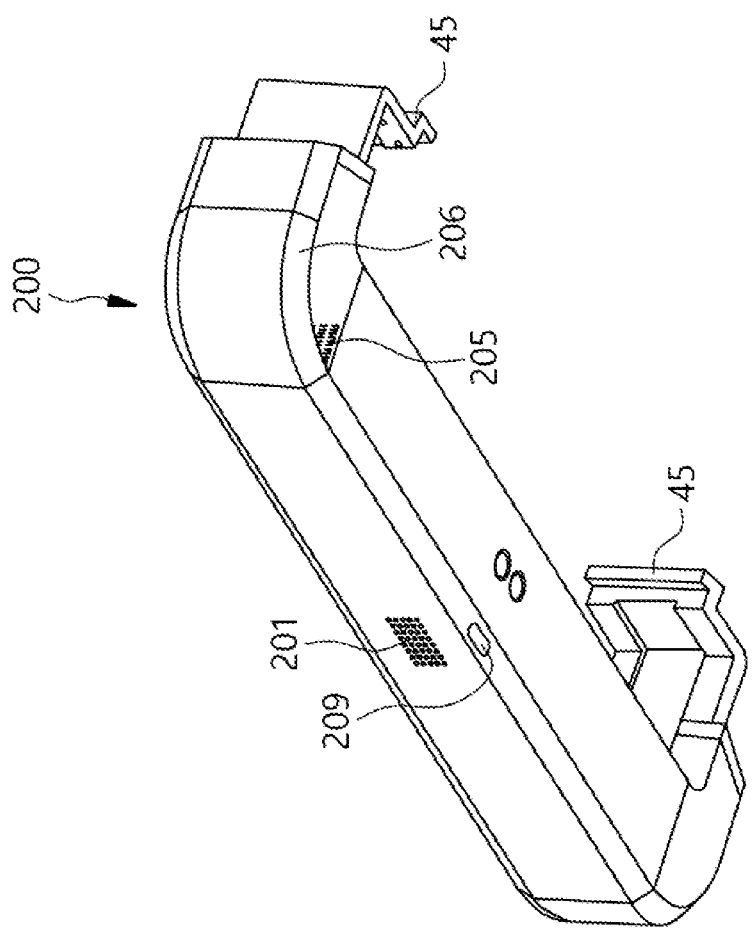
FIG. 15 is a bottom perspective view of the bar of FIG. 14.

FIG. 14 is a top perspective view of the bar 200 according to the embodiment of the invention; FIG. 15 is a bottom perspective view of the bar 200 according to the embodiment of the invention; and FIG. 16 is a rear view of the bar 200 according to an alternative configuration to that illustrated in FIG. 15.

Referring to FIGS. 14 and 15, the bar 200 may include a second air outlet 201 in which forced airflow is expelled at different locations relative to the body 100 depending on the location of the bar 200 relative to the body 100. As described previously in relation to the drive apparatus 11 between the bar 200 and body 100, two guide members 45 may guide the bar 200 in its movement relative the body 100.

One or more air inlets 205 may be located at the ends of the bar 200. The air inlet 205 may be protected in a cavity formed between the end of the bar 200 and a shield 206. The shield 206 may extend from the end of the bar 200 to form a shield at the top and side surfaces thereof except for the bottom surface. The open bottom surface of the shield 206 allows for the air inlet 205 to access inlet air. This configuration may act to prevent drips or splashes of water from entering the air inlet 205. The air inlet 205 provides for inlet air to enter into the bar 200 which houses one or more flow generators 204 (see FIG. 17).

Figure 16:
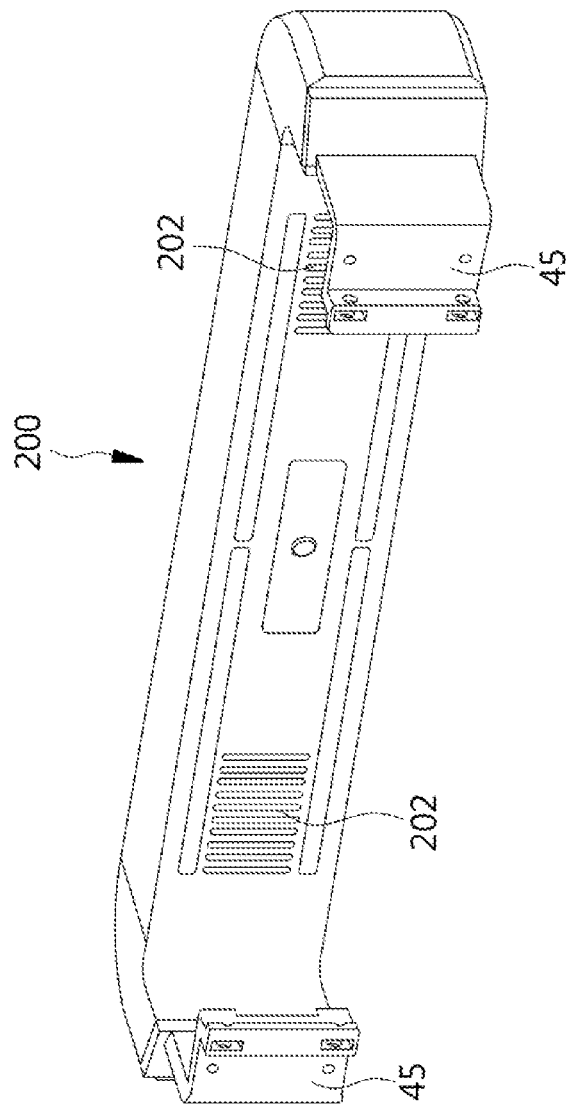
FIG. 16 is a rear view of a bar according to another embodiment of the present invention.

FIG. 16 illustrates two air inlets 202 located at a back side of the bar 200 for supplying air to be vented from the second air outlet 201. In contrast, the air inlets 205 in the configuration of FIG. 15 are located at each end of the bar 200, as explained above. As the bar 200 extends laterally towards a user, more so than the body 100, the bar 200 may be more likely to become wet due to its closer proximity to the user. It may thus be desirable that the one or more air inlets 202 are disposed away from the user. As such, in the configuration of FIG. 16, the air inlets 202 are provided on the back side of the bar 200, as previously explained.

Figure 17:
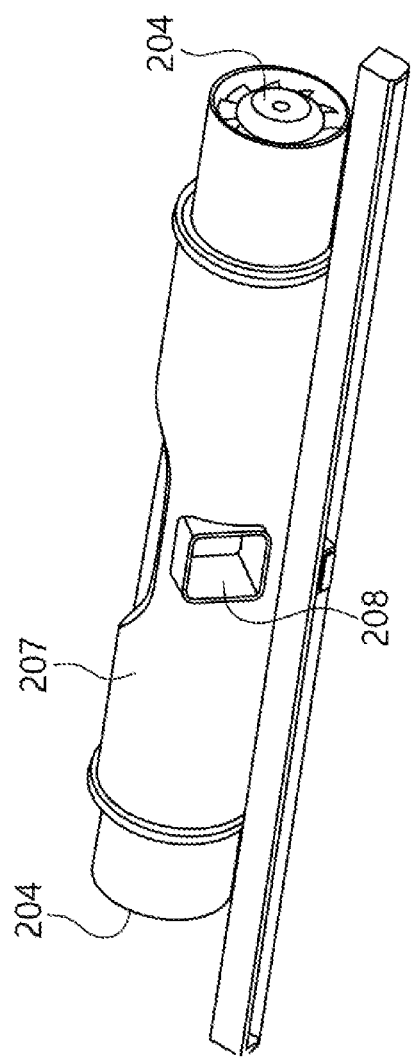
FIG. 17 is a partial view of various internal parts of the bar of FIGS. 14-16 according to an embodiment of the present invention.

FIG. 17 is a partial view of various internal parts of the bar 200 according to an embodiment of the present invention. In particular, FIG. 17 shows the bar 200 with its cover removed to reveal a pair of flow generators 204 and an air conduit 207. The bar 200 may include a pair of flow generators 204 that receives inlet air from the air inlets 202 and generates forced airflow through the air conduit 207. The air conduit 207 may include an intermediate outlet 208 through which the forced airflow may pass and be vented out by the second air outlet 201.

Figure 18:
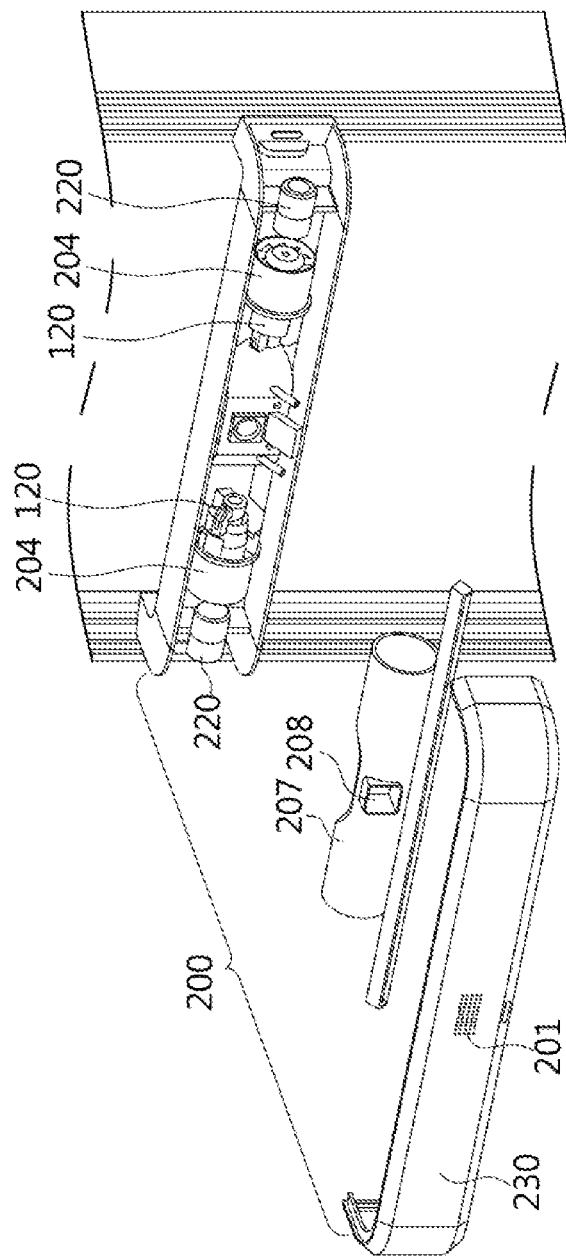
FIG. 18 is an exploded view of various parts of the bar of FIGS. 14-17 according to an embodiment of the present invention.

FIG. 18 is an exploded view showing various parts of the bar 200 according to the embodiment of the present invention described above with respect to FIG. 17.

Referring to FIG. 18, the bar 200 has its cover 230 removed to show various internal parts including a pair of flow generators 204, a pair of motors 220, a pair of thermal devices (for example, resistance heaters, thermoelectric devices, and other suitable devices could be used), and an air conduit 207. The bar 200 has a pair of flow generators 204 which receive inlet air from one or more air inlets (see FIGS. 15 and 16). The pair of flow generators 204 generate forced airflow from the received air which has a relatively high speed. For example, the flow generator may be Smart Inverter Motor™ that sucks in air and expels air at high speed by operating up to 115,000 RPM. However, other types of axial fan assembly may be used.

The forced airflow from the pair of flow generators 204 pass through the air conduit 207 to be expelled from the intermediate outlet 208. The air conduit 207 is shown to be cylindrical but is not limited to this shape and other configurations may be used such as an oval tube, a square tube, a rectangular tube, etc. The air conduit 207 contains the air sucked in by the pair of flow generators 204 within the confines of the air conduit 207 thereby increasing the speed of the forced airflow if not maintaining the speed of the forced airflow expelled by the pair of flow generators 204. Thus, a forced airflow of relatively high speed is introduced into the intermediate outlet 208. The expelled air is ultimately forced out of the second air outlet 201. While the present embodiment illustrates using a pair of flow generators, in other configurations a single flow generator or more than two flow generators may be used.

In the present embodiment, a pair of resistance heaters 120 are shown as part of the bar 200. A resistance heater 120 is located downstream of each of the flow generators 204. In alternative configurations, the resistance heater may be located upstream of the flow generator or may be integrated with the flow generator. In the present embodiment, the flow generators 204 and resistance heaters 120 are at least partially enclosed within the air conduit 207 (see FIG. 17). The air conduit 207 may guide the air heated by the resistance heaters 120 towards the intermediate outlet 208 and out through the second air outlet 201.

While this embodiment uses resistance heaters to heat the inlet air flow, in another exemplary embodiment, a thermoelectric device, for example, using the Peltier effect may be used to heat or cool the inlet air flow. In this configuration, the bar 200 is not limited to expelling heated air but may also expel cold air.

The bar 200 may further comprise one or more motors 220. As shown in FIG. 18, one or more motors 220 may be provided along a longitudinal axis of the bar 200 which may be parallel to the drying face 14 of body 100. The one or more motors 220 may cause the bar 200 to tilt up or down by rotating about its longitudinal axis. By tilting the bar 200 up or down, the bar 200 may expand the coverage area to which the forced airflow may be applied. Also, by tilting the bar 200 up and down continuously while blowing forced air, the bar may enhance drying performance.

Figure 19:
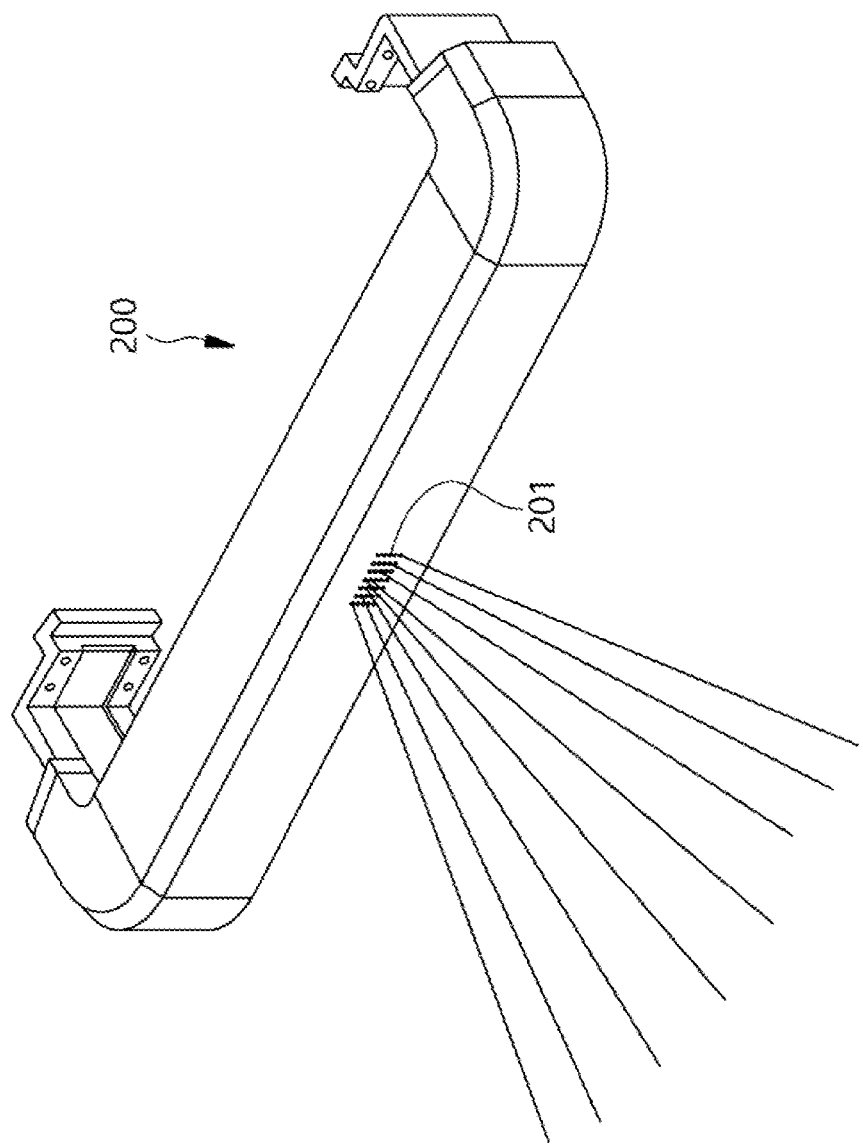
FIGS. 19 and 20 are views showing exemplary ways in which forced air may be expelled from the bar of FIGS. 14-18 according to embodiments of the present invention.
Figure 20:
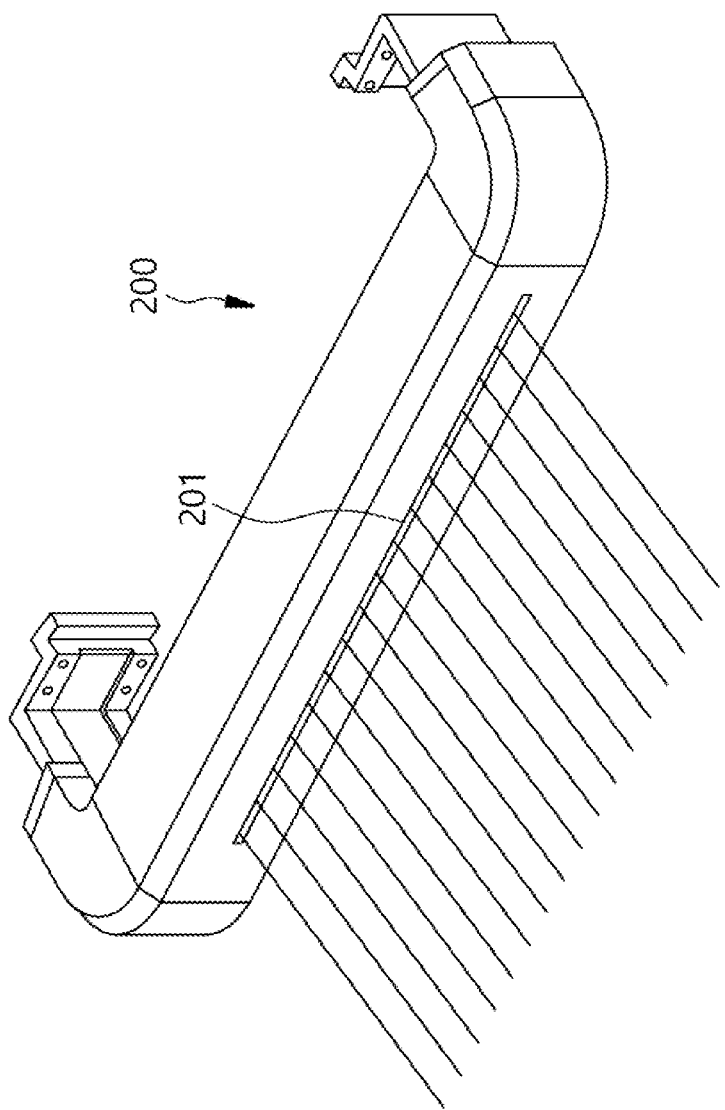

FIGS. 19 and 20 are views illustrating exemplary ways in which forced air may be expelled from the second air outlet 201, according to exemplary embodiments of the present invention, based on the shape and/or size of the second air outlet 201.

The second air outlet 201 may be configured such that the expelled airflow may cover a width of the user as the bar 200 moves up or down along the length of the user. The bar 200 may be provided with a suitable second air outlet 201 that may direct the forced airflow across the full width of the user.

Referring to FIG. 19, more specifically, the second air outlet 201 may be configured to provide a laterally expanding forced airflow. As the forced airflow flows further away from the second air outlet 201, the forced airflow expands at least horizontally to better cover a width of the user's body. An example of a structure to form an expanding forced airflow is shown in FIG. 18.

The intermediate outlet 208 of the air conduit 207 may be a circular, oval, or quadrilateral air outlet from which the forced airflow may fan out as the air flow travels further from the second air outlet 201. As an example, a circular air outlet may form a relatively narrow but relatively strong forced airflow over a small area of the user's body. A rectangular air outlet may form a relatively wider but relatively weaker forced airflow over a larger area of the user's body.

The degree to which the forced airflow fans out may be determined by the angle of the arc at the intermediate outlet 208. As an example, a narrow arc may form a narrow but strong airflow covering a small part of the user's body. A wider arc may form a wider but weaker airflow covering a wider part of the user's body. The shape of the intermediate outlet 208 and the angle of the arc may be selected depending on a desired effect of the forced airflow over the user's body.

Referring now to FIG. 20, the second air outlet 201 may alternatively be an elongated slit across the longitudinal length (in the lateral direction relative to the longitudinal length of the body) of the bar 200 to expel a planar blade of outlet air. In one configuration, the length of the slit may be sufficient to cover a width of the user's body. In this configuration, as the bar 200 travels vertically up and/or down with respect to the body 100, the forced airflow of the second air outlet 201 may cover all parts of the user's body. For this configuration, the intermediate outlet 208 may be formed as an elongated slit running across the longitudinal length of the air conduit 207. The second air outlet 201 being an elongated slit as shown in FIG. 20 corresponds to the slit of the intermediate outlet 208.

Figure 21:
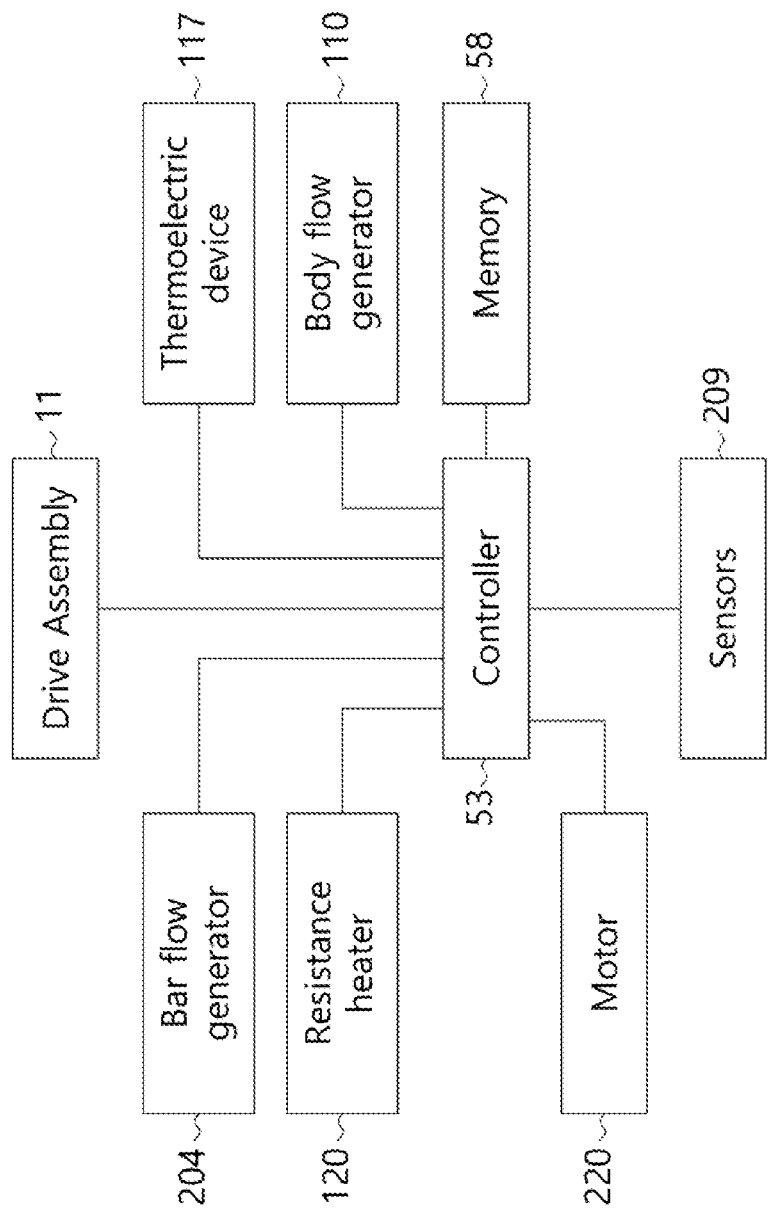
FIG. 21 is an electrical schematic diagram of the drying apparatus according to an embodiment of the present invention.

FIG. 21 is an electrical schematic diagram of a drying apparatus 10 according to an embodiment of the present invention. A controller 53 controls the overall operation of the drying apparatus 10. The controller 53 may be a microprocessor, an integrated circuit, an electrical circuit, a logical electrical circuit, and the like.

The controller 53 may control the operation of the body flow generator 110 and the thermoelectric device 117 of the body 100; the controller 53 may control the operation of the flow generator 204 and the resistance heater 120 associated with the bar, and may control the motor 220, among others. The various operations which are performed by the components have been described above and further description will be omitted. The controller 53 may access or store information in a memory 58 for controlling the operation of the drying apparatus 10.

The drying apparatus 10 may include one or more sensors 209 which are also controlled by the controller 53. These sensors 209 may variously be associated with the body 100 and the bar 200 (e.g., FIGS. 12C and 15). In some embodiments, one or more sensors 209 may be located remotely from the drying apparatus 10.

According to various embodiments, such as the embodiments shown in FIGS. 12C and 15, for example, the one or more sensors 209 may be associated with the bar 200. The controller 53 may receive sensor information from the one or more sensors 209 of the bar 200 and the controller 53 may operate the drying apparatus 10 utilizing the sensor information as an operation parameter.

As an example, sensing information of the one or more sensors may be utilized by the controller 53 to determine various characteristics of the environment surrounding the apparatus and/or various characteristics and/or conditions of a user. For example, the sensing information may be utilized to determine the presence of a user; physical characteristics of the user including their overall and/or particular dimensions; wetness of a user's body and/or different parts of their body; temperature or heat of the ambient air and/or humidity of the ambient air, among others. To achieve this, the drying apparatus 10 may include one or more sensors 209 described below.

The one or more sensors 209 may include a thermal sensor such as an infrared sensor. The infrared sensor may be used to obtain information on the heat of the surroundings. For example an infrared sensor may be used as a temperature sensor to sense the temperature of the ambient air. Information on the temperature of the ambient air may be obtained to determine whether to condition the ambient air.

The infrared sensor may be used on a user's body located adjacent to the drying apparatus 10. Information from the infrared sensor may be utilized to infer or determine moisture levels of the user's body, and/or specific parts of the user's body. Information from the infrared sensor may be utilized to obtain an indication of the overall dimensions of a user's body, where body temperature differs from the temperature of the surrounding air.

The one or more sensors 209 may include a proximity sensor. The proximity sensor may be utilized to determine the proximity of the user to the drying apparatus 10. For example, information from the proximity sensor may be utilized to determine the distance of the user from the drying face 14 of the drying apparatus 10. When the user is within a predetermined distance of the drying face 14, the drying apparatus may be activated to dry the user. Information from the proximity sensor may utilized to control a forced airflow speed from the air outlet 101 and/or the air outlet 201 dependent on the distance of the user, in order to obtain a desired forced airflow speed directed at the user.

The proximity sensor may be utilized to determine if a user is undesirably close to the drying apparatus or a part thereof. For example, for safety reasons, it may be desirable to limit or prevent the movement of the bar 200 when a person is within a particular distance or position relative to it. This may include where part of a person's body is located above or below the bar 200, within its path of movement.

The one or more sensors 209 may include an image sensor. The image sensor may be utilized to obtain image information of the surroundings, determine the presence of a user, and determine overall dimensions of a user's body and/or specific parts of the user's body. The image sensor may be used in conjunction with or in lieu of the thermal sensor for information such as those mentioned above in order to obtain a more accurate information.

The one or more sensors 209 may include a humidity sensor. The humidity sensor may also be utilized to obtain information on the humidity of surrounding ambient air, for example, a humidity level of the bathroom in which the drying apparatus is installed. The drying apparatus 10 may be activated or used to remove moisture in the air until the humidity level is below a predetermined level. The humidity sensor may also be utilized to obtain information regarding the level of wetness/dryness of the user's skin. The information may be used to control heat applied to the forced airflow so that the user's skin does not become too dry.

Besides the exemplary sensors described above, other sensors known in the art may be used to achieve a desired result.

As previously mentioned, the drying apparatus 10 may perform air conditioning of a given space. For example, the space may be a bathroom. During hot days, the drying apparatus 10 may cool the bathroom and during cold days the drying apparatus 10 may heat the bathroom for the comfort of the user. In such a scenario, the controller 53 may determine the ambient temperature or ambient heat level of the bathroom, and use this information to control the temperature to the satisfaction of the user.

For example, in a hot bathroom, the user may perspire to keep cool. The perspiration evaporates taking some of the heat from the user's body providing a sensation of coolness. However, when the humidity level is high in the bathroom, the perspiration does not evaporate as efficiently and thus remains as moisture on the user's body. This may cause discomfort to the user as the user feels hotter than the temperature of the bathroom.

Accordingly, the controller 53 in conditioning the bathroom may need to consider the temperature as well as the humidity. In one embodiment, the controller 53 may consider a comfort level index correlating temperature and humidity to determine user comfort. The temperature-humidity index (THI), also known as the discomfort index, may be used to determine a comfort sensation with respect to the current sensed temperature and the current sensed humidity.

There are several equations devised to determine THI. One equation may be:

$$THI = T_d - (0.55 - 0.55RH)(T_d - 58)$$

where $T_d$ is the dry-bulb temperature in ° F., and RH is the relative humidity in percent, expressed in decimal. For example, 50% relative humidity is 0.5.

It should be noted that the THI is not absolute but relative. Temperatures affect people differently. Various factors such as height, weight, sex, health condition, etc., may cause one person to feel temperature differently than another person.

Below is a table that illustrates a THI which reflects the comfort level of a typical person.

| Level | THI Range | Comfort Level |
|---|---|---|
| Very High | Above 80 | Everyone experiences discomfort |
| High | Between 75 and below 80 | 50% experiences discomfort |
| Normal | Between 68 and below 75 | Discomfort begins to be felt |
| Low | Below 68 | No discomfort is felt |

Figure 22:
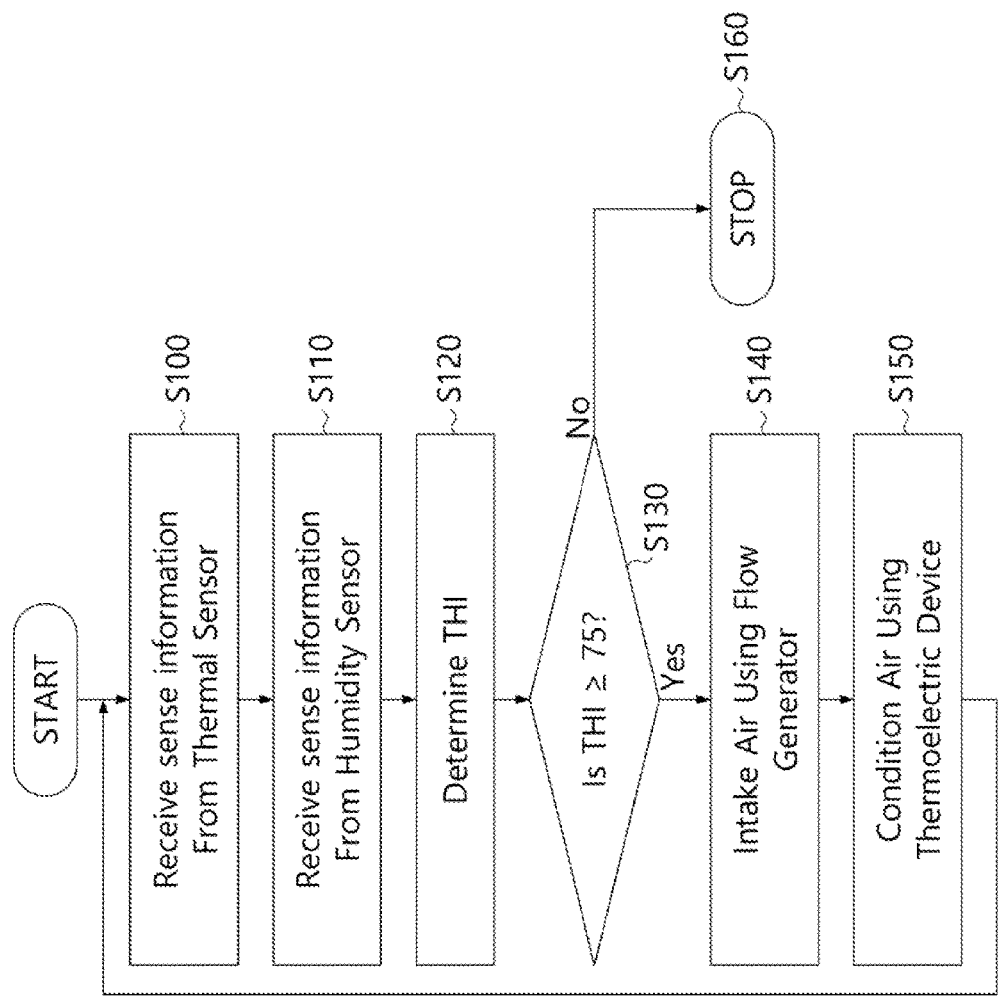
FIG. 22 is a flowchart for control of temperature-humidity index (THI) by a controller according to one embodiment of the present invention.

FIG. 22 is a flowchart illustrating a method for controlling temperature of a given space using a temperature-humidity index (THI), by a controller, according to one embodiment of the present invention.

Referring to FIG. 22, in step S100, the controller 53 may receive sense information from the thermal sensor. The information may be an ambient temperature of the bathroom. In step S110, the controller 53 may receive sense information from the humidity sensor. The information may be a humidity level of the bathroom. In step S120, the controller 53 may use the received temperature information and the humidity level information to determine the THI. One equation that the controller 53 may use to derive the THI may be the equation provided above. The equation may be stored in the memory 58 to be accessed by the controller 53.

In step S130, the controller 53 may determine whether the derived THI is greater than or equal to 75. The reference index of 75 may be stored in the memory 58. It should be noted that the reference index of 75 is not absolute. For example, the reference index of 75 may be increased or decreased in the memory 58 to tailor to individual user's need. If the THI is less than 75 the controller 53 may continue to step S160 where the controller 53 may terminate the control of the THI.

Otherwise, in step S130, if the controller 53 determines that the THI is greater than or equal to 75, the controller 53 may continue to step S140. In step S140, the controller 53 may send a signal to activate the flow generator. The flow generator may be either on or off, i.e., producing a constant air flow. Alternatively, the controller 53 can be configured to control a variable air intake amount by using an air intake amount value corresponding to the desired air flow. For example, the flow generator may be the flow generator 110 located at the body 100. At step S150 the controller 53 may activate the thermoelectric device 117. It should be noted that the activation of the flow generator and the thermoelectric device need not be in sequence; it can be simultaneous or in reverse order.

The controller 53 may send a signal to the thermoelectric device 117 to cool (or warm) the air sucked in through the air inlet 102. The cooled air may reduce the temperature of the intake air as well as dehumidify the air. The cooled, dehumidified air may then be expelled through the air outlet 101. The controller 53 may be configured to adjust the amount of heating or cooling via a heat level value. The heat level value can correspond to a heat level, either cooler or hotter than the ambient air. The controller 53 continues to step S100 to repeat steps S100 to S130.

At step S130, the controller 53 may again determine whether the THI is greater than or equal to 75. If the controller 53 again determines that the THI is greater than or equal to 75, the controller 53 continues to steps S140 and S150 and continues to intake air and to cool the air. The controller 53 continues unless and until the controller 53 determines at step 130 that the THI is less than 75. In which case, the controller 53 continues to step S160 where the controller 53 terminates the method.

In some instance, the forced airflow provides a wind chill to the user, which the system can also use as a comfort level to adjust air intake and temperature. This is where the user perceives the airflow at a temperature lower than that of the ambient air temperature. There are several equations devised to determine wind chill. For the purpose of this disclosure, reference may be made to the North American and UK wind chill index as follows:

$$T_{wc} = 13.12 + 0.6215 T_a - 35.75 v^{+0.16} + 0.4275 T_a v^{+0.16}$$

where $T_{wc}$ is the wind chill index, based on the Celsius temperature scale; $T_a$ is the air temperature in degrees Celsius; and v is the airflow speed in kilometers per hour.

Based on the above equation, the higher the forced airflow speed the lower the perceived temperature of the air flow by the user. Thus, when airflow speed increases the controller 53 may increase the temperature of the forced airflow to obtain the target temperature.

Embodiments may not have a sensor to determine the airflow speed, but can estimate it due to known constraints within the system. For example, the size of chambers for airflow, the power of the air flow generator, and the size of the outlet for the airflow are all known variables. Therefore, embodiments include estimating the airflow speed based on these known parameters. Embodiments may also include a table that correlates airflow speed with the speed at which the airflow generators operate. Therefore, for a known air flow generator input, the system may know the airflow speed based on corresponding predetermined values. In one embodiment, the target surface skin temperature of the user may be about 30 to about 32 degrees Celsius. Thus forced airflow heating or cooling may be provided to maintain or obtain this temperature.

In one embodiment the temperature of the forced airflow generated by the drying apparatus 10 should be at a temperature that provides little or no discomfort to the user. The Humidex index of apparent temperature may provide a suitable guide on the level of comfort or discomfort provided by a temperature applied to a user's skin. The Humidex index takes into account both temperature and relative humidity in determining the level of comfort or discomfort. The humidex formula is as follows:

$$H = T_{air} + \frac{5}{9}\left[6.11 e^{5417.7530\left(\frac{1}{273.16} - \frac{1}{273.15 + T_{dew}}\right)} - 10\right]$$

Where H denotes the Humidex, $T_{air}$ is the air temperature in ° C., and $T_{dew}$ is the dew point in ° C.

In some embodiments, the apparent temperature to be applied to the user is between 20 to 39° C. In a preferred embodiment, the apparent temperature to be applied to the user is between 20 and 29° C. As mentioned above, the apparent temperature may be determined by taking into account the wind chill factor of the airflow temperature.

Figure 23:
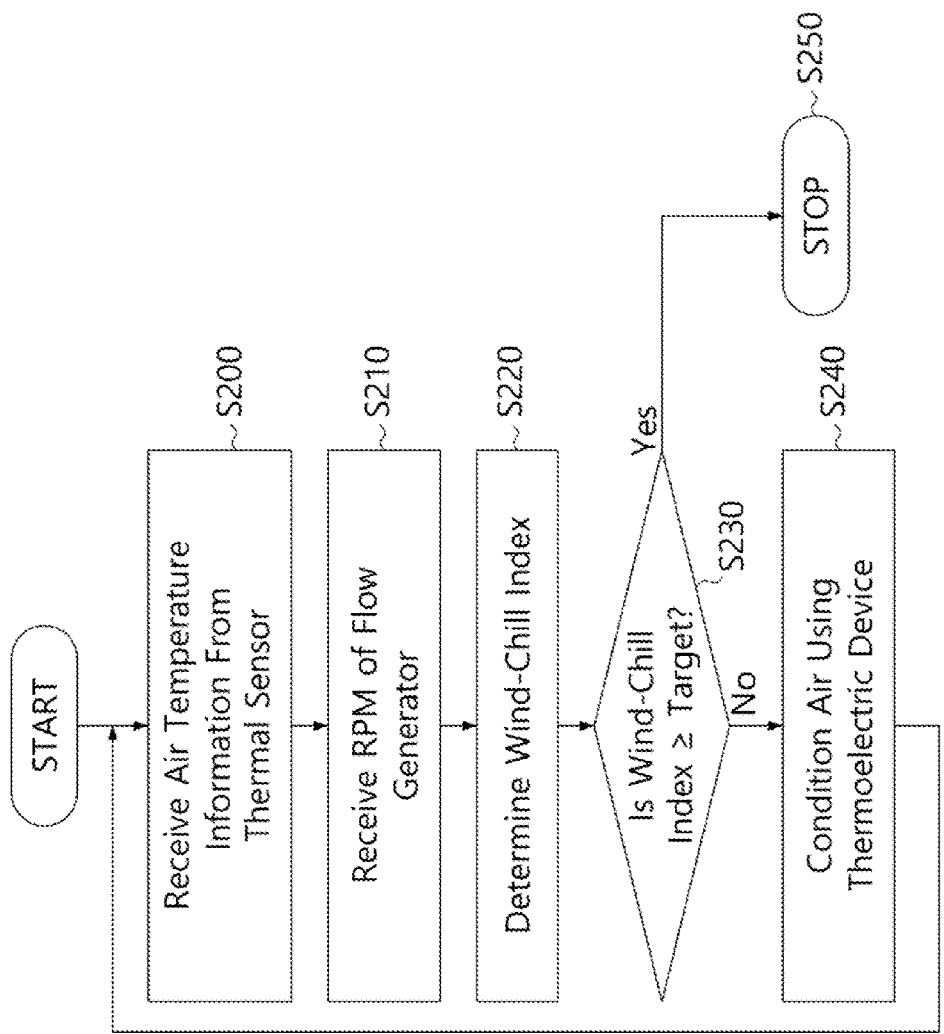
FIG. 23 is a flowchart for control of wind chill index by a controller according to one embodiment of the present invention.

FIG. 23 is a flowchart illustrating a method for controlling temperature using a wind chill index, by a controller, according to one embodiment of the present invention.

Referring to FIG. 23, the controller 53 may control the flow generator 204 to direct forced airflow to the user's body through the air outlet 201 based on the thermal sensor information and a wind-chill index. At step S200, the controller 53 receives information from the thermal sensor. The information may for example, reflect an air temperature in the vicinity of the bar 200, if the thermal sensor location is the location of sensor 209 as shown in FIG. 15.

In step S210, the controller 53 receives the revolutions per minute (RPM) of the flow generator 204. In this configuration, the RPM of the flow generator 204 is variable. In a configuration where the flow generator 204 is not variable, but fixed, the controller 53 may retrieve the RPM stored in the memory 58. The RPM of the flow generator 204 is equated to an airflow speed of the forced airflow.

In step S220, the controller 53, having the air temperature at the bar 200 and the airflow speed of the forced airflow, may determine the wind chill index. One equation that the controller 53 may use to derive the wind chill index may be the equation provided above. The equation may be stored in the memory 58 where it is accessed by the controller 53.

In step S230, the controller 53 determines whether the derived wind chill index is greater than or equal to a predetermined target. The predetermined target may be chosen from among many different temperatures or temperature ranges. For example, the target may be the target surface skin temperature of about 30 to about 32 degrees Celsius. The target may be stored in the memory 58.

If the wind chill index is less than the target, the controller 53 may continue to step S240. In step S240, the controller 53 may increase the temperature of the forced airflow by heating the air flow using the resistance heater 120 at the bar 200, for example. The controller 53 may continue to step S200 and then repeat steps S200 to S230. Since the thermal sensor is close to the air outlet 201, the thermal sensor may sense an increase in temperature. Also, step S210 may be skipped where the RPM of the flow generator does not change.

As indicated, the controller 53 repeats the process unless and until the controller 53 determines, at step S230, that the wind chill index is greater than or equal to the target. If the wind chill index is greater than or equal to the target, the controller 53 continues to step S250, deactivates the resistance heater 120 and terminates the method.

Figure 24A:
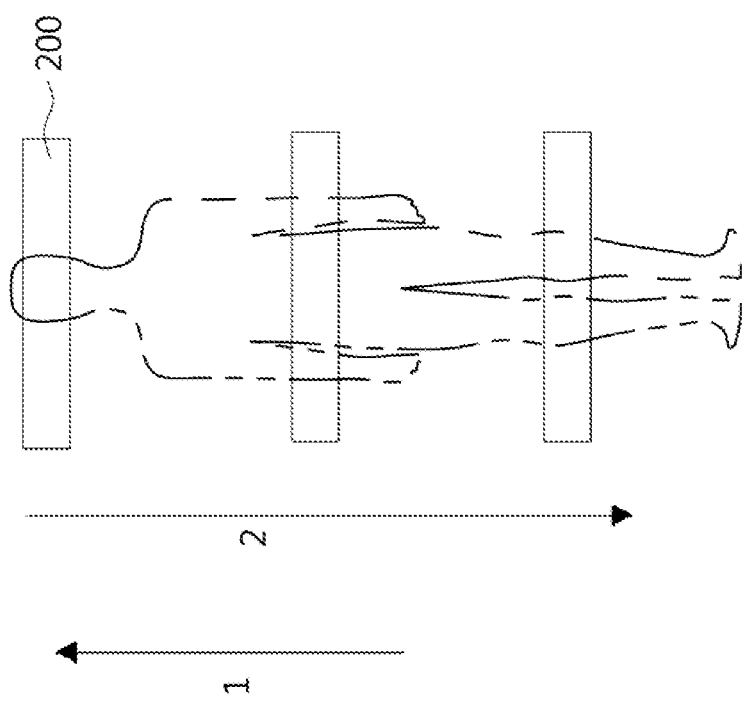
FIGS. 24A and 24B are views showing a user being dried with the bar of the drying apparatus according to an embodiment of the present invention.
Figure 24B:
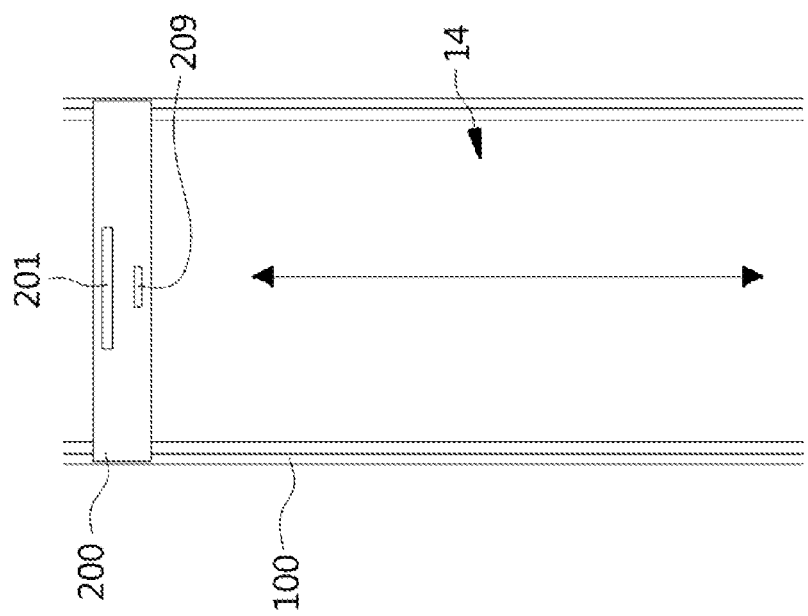

FIGS. 24A and 24B are views illustrating a user being dried by the bar 200 of the drying apparatus 10 according to an embodiment of the present invention.

Referring to FIGS. 24A and 24B, the bar 200 includes sensor 209 which may be a thermal sensor positioned such that it faces the user when the user is present at the drying face 14 of the body 100. While the bar 200 may be located at any position along the longitudinal length L1 of the drying face 14 of the body 100, in the present embodiment the starting position of the bar 200 may be somewhere approximating a middle portion of the drying face 14. When the drying apparatus 10 is activated, the bar 200 may be driven upward by the drive apparatus 11 in the direction of arrow 1. Coincidently, the thermal sensor may be activated.

As the bar 200 is driven upward, the thermal sensor scans the user. When the thermal sensor no longer detects thermal heat from the user, then the height of the user is determined to have been reached and the drive apparatus 11 may stop the movement of the bar 200. The drive apparatus 11 now may move the bar 200 downwards in the direction of arrow 2. At the same time the thermal sensor scans the user. The thermal sensor may operate to detect wetness at the part of the user being scanned. The thermal sensor may detect wetness on the user as being a cooler temperature and dryness as being a warmer temperature. The flow generator 204 and perhaps the resistive heater 120 may be activated to dry the user.

In another configuration, the flow generator 110 and perhaps the thermoelectric device 117 may be activated to dry the user. The flow generator 110 and the thermoelectric device 117 may be operated in combination with the operation of the flow generator 204 and the resistive heater 120 of the bar 200. The flow generator 110 and the thermoelectric device 117 may be continuously operated until the bar 200 has reached the bottom of the drying face 14 and then the flow generator 110 and the thermoelectric device 117 may be deactivated.

As shown in FIG. 24B, the bar 200 may be positioned by the head of the user. Because hair usually retains a lot of water, the thermal sensor may detect significant wetness when the bar 200 is in this position. Accordingly, the bar 200 may not move while the second air outlet 201 expels heated forced airflow to dry the user's head. When the thermal sensor detects that the user's head is sufficiently dry the drive apparatus 11 may move the bar 200 downwards in the direction of the arrow 2.

As the bar 200 moves downward in the direction of the arrow 2, the heated forced airflow expelled from the second air outlet 201 may dry the head, the body, and eventually the legs. While the bar 200 is transitioning from the head to the legs, the bar may stop, dry parts of the user which are more wet than other parts, before moving further down in the direction of arrow 2, until the bar 200 has reached to the bottom of the drying face 14.

In another embodiment, the bar 200, after initially reaching the head of the user, may move up and down repeatedly from head to toe until the thermal sensor senses that the user is dry. The movements of the bar described are exemplary and other forms of movement of the bar to dry the user may be conceived.

Figure 25:
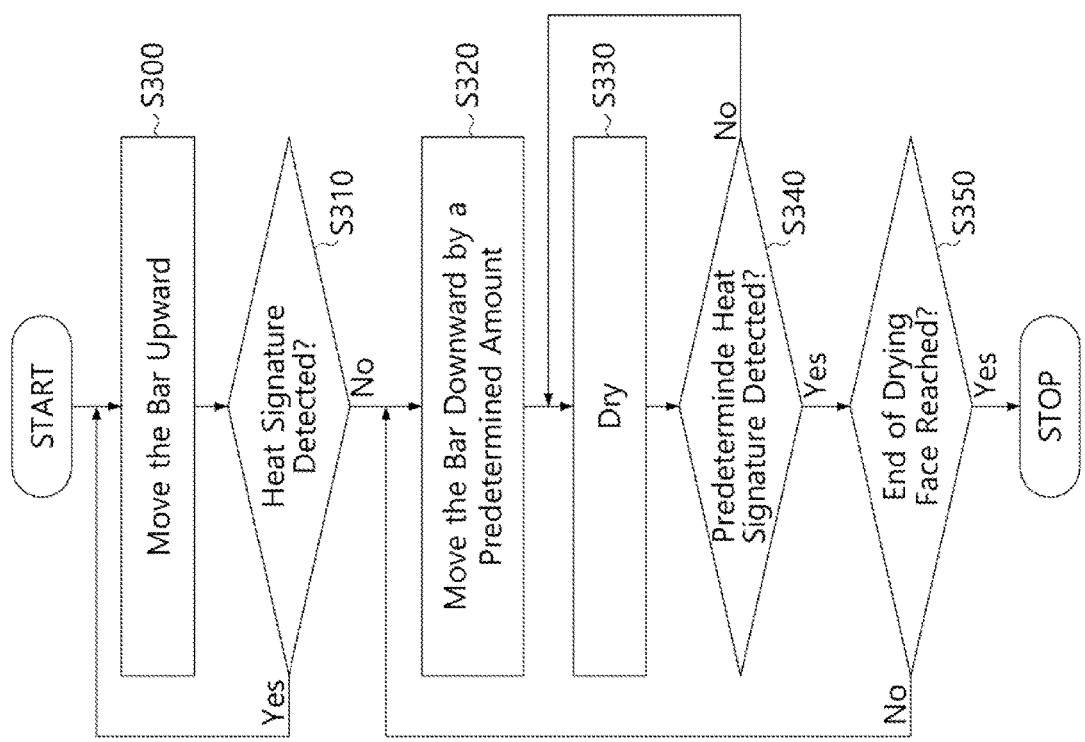
FIG. 25 is a flowchart for drying of a user by the controller according to an embodiment of the present invention.

FIG. 25 is a flowchart illustrating an exemplary method for drying a user, by the controller, according to an embodiment of the present invention.

Referring to FIG. 25, in step S300, the controller 53 moves the bar 200 upward with respect to the body 100. The controller 53 also receives heat information from the thermal sensor. In step S310, the controller 53 determines whether the thermal sensor detects heat. If the thermal sensor detects heat, the controller 53 continues to move the bar 200 upward in step S300. Otherwise, if the thermal sensor does not detect heat, the controller 53 stops the movement of the bar 200, on the assumption the bar 200 has reached the height of the user, and continues to step S320.

In step S320, the controller 53 moves the bar 200 downward by a predetermined amount, such as one width of the user's body covered by the forced airflow from the bar 200. In step S330, the controller 53 operates the flow generator 204. In this step, the controller 53 may also activate the flow generator 110 and perhaps the thermoelectric device 117. Thus forced airflow from the air outlet 201 may dry a corresponding part of the user adjacent to the bar 200. Also, the forced airflow from the air outlet 101 may aid in the drying of the user. The controller 53 then continues to step S340.

In step S340, the controller 53 determines whether the thermal sensor detects heat greater than or equal to a predetermined amount. The predetermined amount may indicate that the part of the user is sufficiently dry. If the thermal sensor detects heat less than the predetermined amount, the controller 53 continues with step S330 where the controller 53 continues to dry corresponding the part of the user. Otherwise, the controller 53 continues to step S350.

In step S350, the controller 53 determines whether the bar 200 has reached the bottom of the drying face 14 of the body 100. If the bar 200 has not reached the bottom of the drying face 14, the controller 53 continues to step S320, and repeats steps S320 to S340. Otherwise, if the bar 200 has reached the bottom of the drying face 14, the controller 53 deactivates the flow generator 204 and the resistance heater 120. If the flow generator 110 and the thermoelectric device 117 were activated, the controller 53 deactivates these as well.

Figure 26:
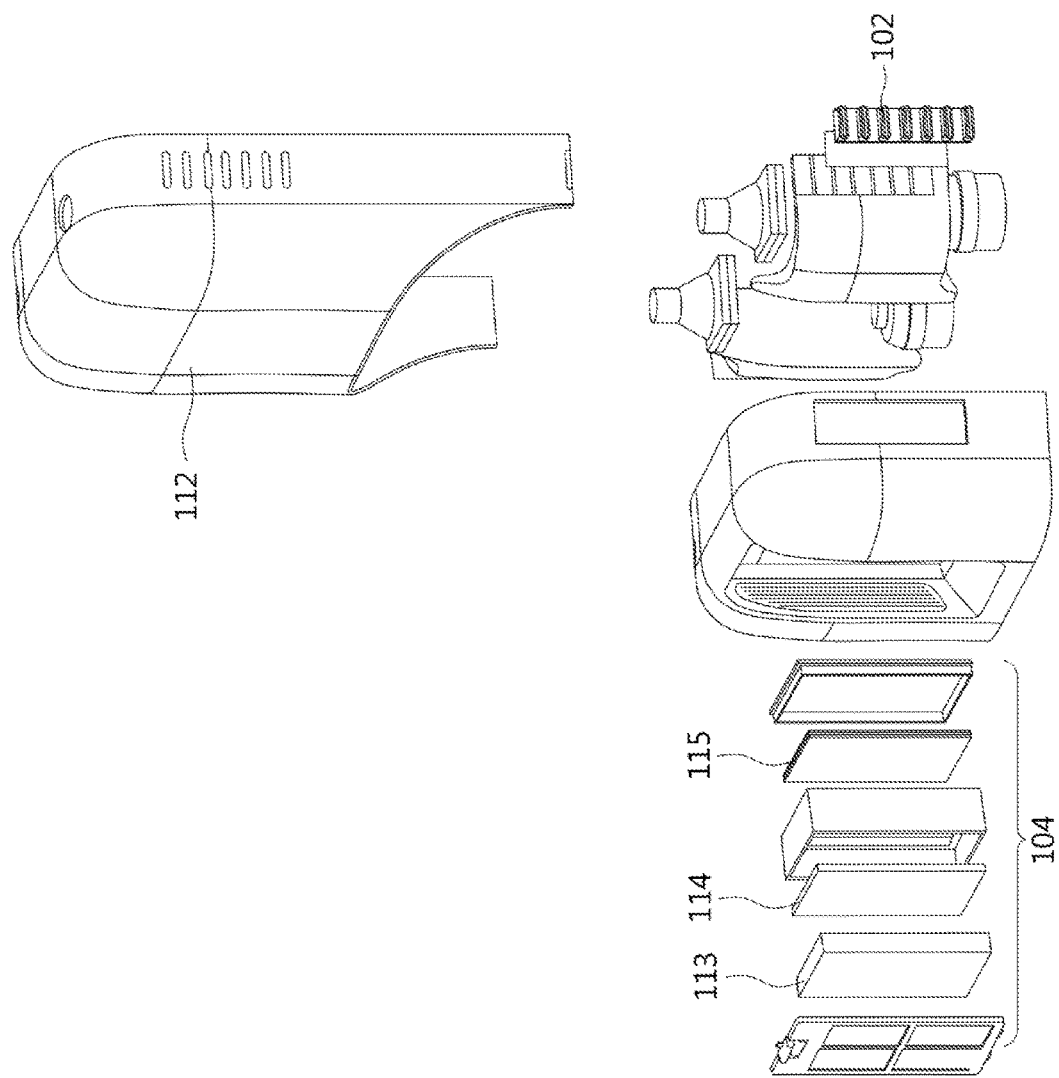
FIG. 26 is an exploded view of an upper region of the drying apparatus showing an exploded view of a filter unit according to an embodiment of the present invention.
Figure 27:
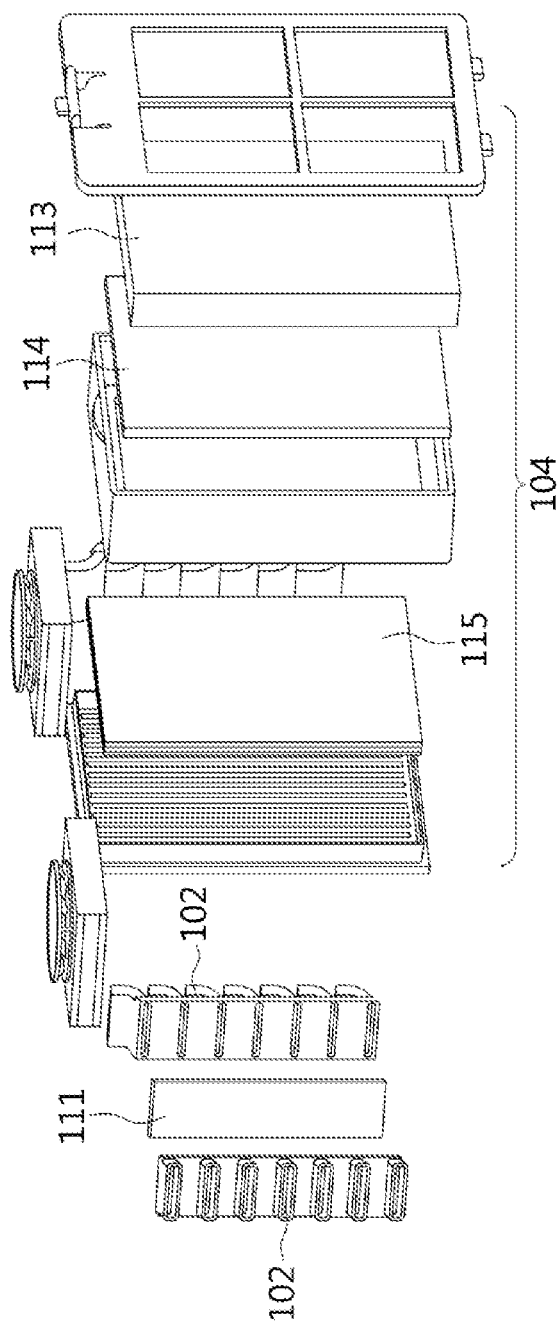
FIG. 27 is another exploded view of the filter unit of FIG. 26 according to an embodiment of the present invention.

FIG. 26 is an exploded view of an upper region of the drying apparatus 10 illustrating an exploded view of a filter unit according to an embodiment of the present invention; and FIG. 27 is another exploded view of the filter unit according to an embodiment of the present invention.

The filter unit 104 may provide one or more filtrations or treatments to inlet air flow. Ambient air, particularly in cities or other urban settings, may contain undesirable levels of particulate matter. Such particulate matter may be harmful to a person's health, and may also have undesired effects on a person's skin if blown onto the person when using the drying apparatus to dry their body.

For example, particulate matter may be either basic or acidic, and thus cause damage to a user's body. The filter unit 104 may comprise one or more particulate filters 113, such as is seen in FIG. 27, to capture particulate matter. The one or more particulate filters 113 may be in the form of any commonly available filter, for example, a fiberglass filter, a polyester filter, or a High Efficiency Particulate Air (HEPA) filter.

Ambient air is also likely to contain bacteria and viruses, which may pose a risk of infection to a user of the drying apparatus. If not entrained by a particulate filter 113, a filter unit 104 may include a bacterial and/or viral filter 114. Such a filter may include antimicrobial or antibacterial elements.

It may be desirable to reduce or remove moisture in inlet air before it is vented for drying. The filter unit 104 may include one or more dehumidifying filters 115, having for example a desiccant material.

In the present embodiment, a pair of air inlets 102 each pass the inlet air to the filter unit 104. The use of a single filter unit 104 may be desirable particularly where there are multiple flow generators to provide for a single point of servicing of any filters within the filter unit.

Figure 28:
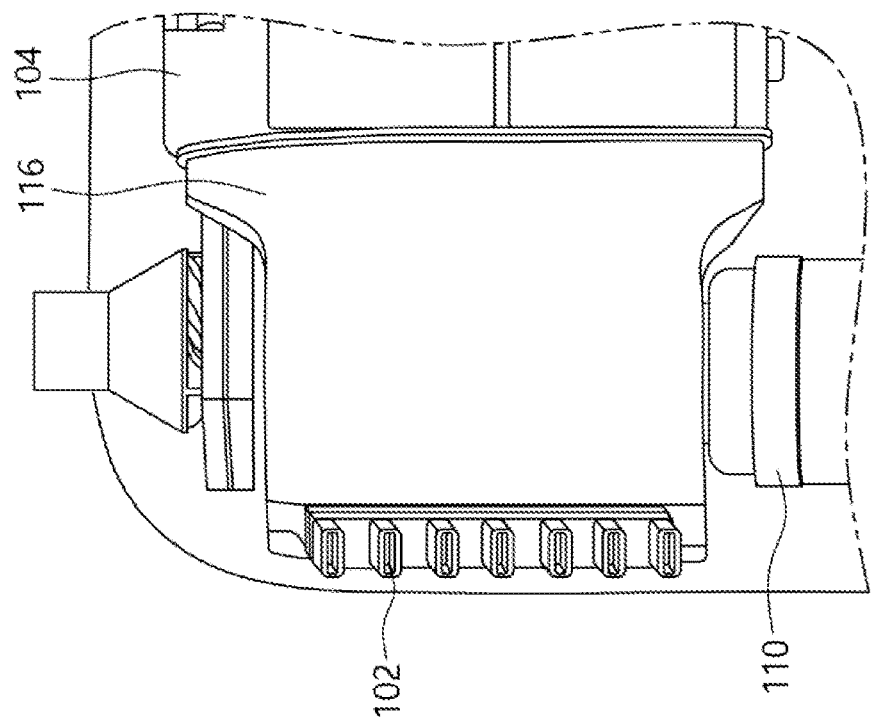
FIG. 28 is a front view of an air inlet and an inlet pathway at a flow generator housing according to an embodiment of the present invention.
Figure 29:
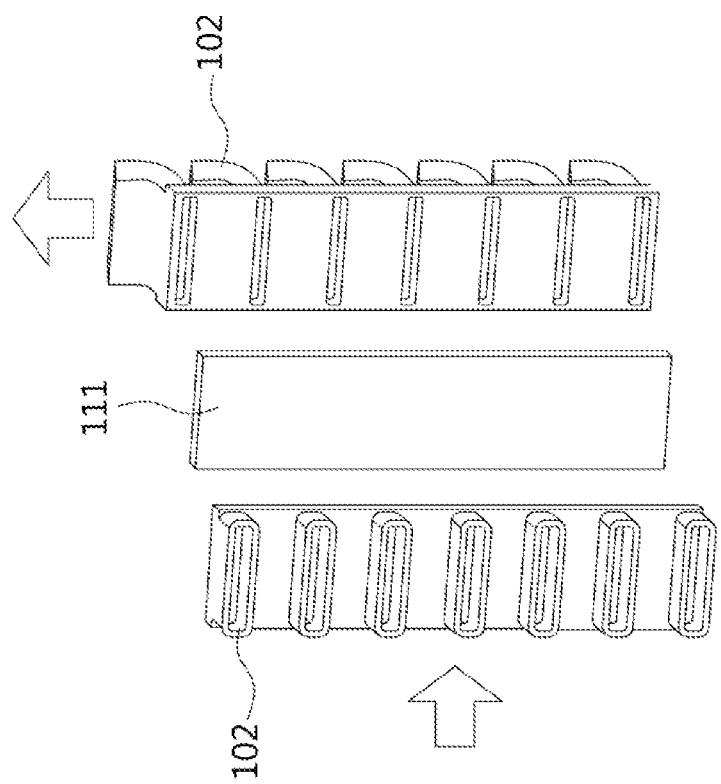
FIG. 29 is a partial exploded view of the air inlet of FIG. 28.

FIG. 28 is a front view of an air inlet and an inlet pathway at a flow generator housing according to an embodiment of the present invention; and FIG. 29 is an exploded view of the air inlet of FIG. 28.

Referring to FIG. 28, an inlet pathway, which involves the air inlet 102 and the flow guide 116, directs inlet air from the air inlet 102 to the filter unit 104. However, because the drying apparatus 10 may be used in a wet environment, such a bathroom or shower, water may be splashed onto the drying apparatus 10 or into the air surrounding the drying apparatus 10, including the air inlets 102. Additionally, in use, there may be suction at the air inlets 102 due to operation of the flow generators 110 which could pull nearby water into the air inlets 102. It is undesirable that such water enters the drying apparatus 10. In addition to water making its way into the air inlets 102, the flow path may intake other matter passing through the air inlets 102 and into the flow guide 116.

As shown in FIGS. 28 and 29, the air inlets 102 provide for an upwardly deflected flow path into the flow guide 116. This upward deflection may act as a gravitational barrier to the ingress of water or other solid objects into the drying apparatus 10. To further prevent unwanted water or other matter passing into the flow path, an obstruction in the inlet flow path may additionally or alternatively be provided in the form of an inlet filter 111, for example as seen in FIG. 29. This inlet filter 111 may, more specifically, be in the form of a particulate filter, for filtering particles from the inlet air.

Alternatively the inlet filter 111 may be in the form of a macroscopic filter, such as a macroscopic mesh filter for guarding against the inletting of larger matter. Where it is desired to guard against water being drawn in with the inlet air or to dehumidify the inlet air the inlet filter 111 it may include a desiccant material for absorbing water.

As a further measure to dehumidify the inlet air, a resistance heater (not shown) may be placed adjacent to the inlet filter 111. When operated, the resistance heater may heat the inlet air to remove moisture in the air. Further, the resistance heater may remove moisture in the inlet filter 111 to increase the life of the inlet filter 111.

Figure 30:
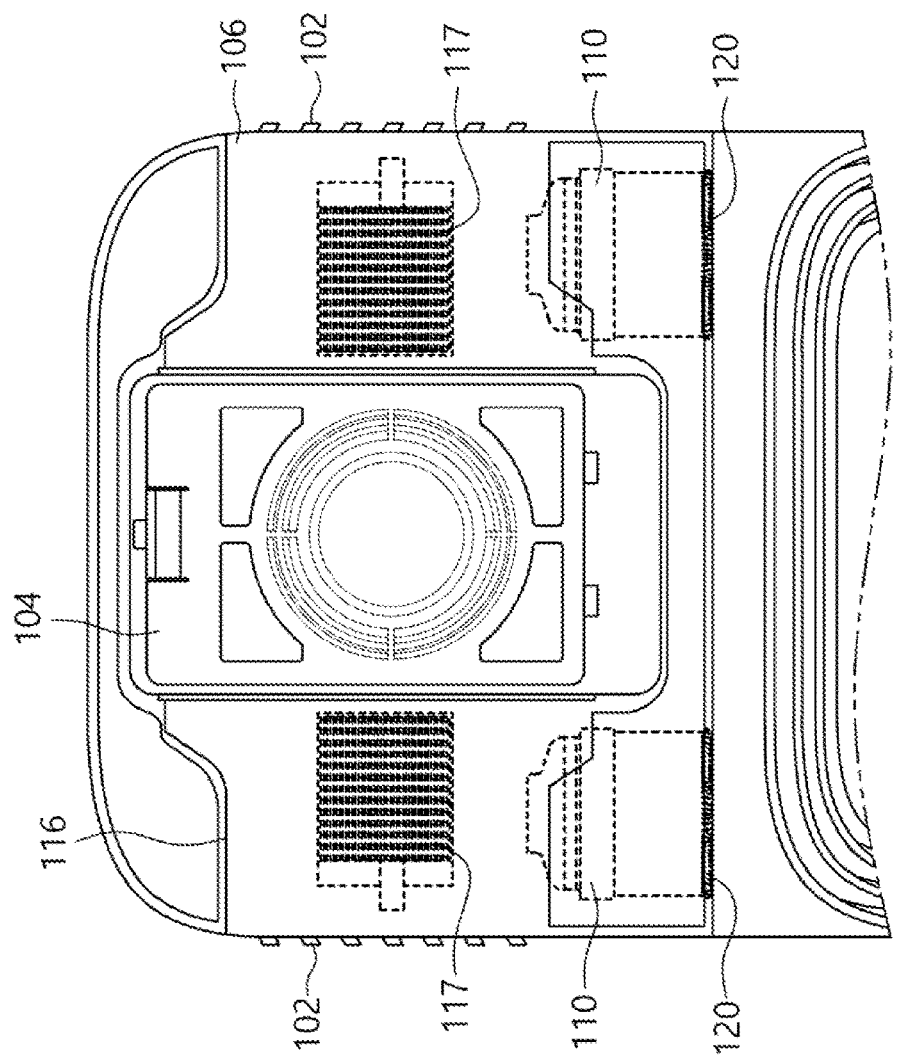
FIG. 30 is a front transparent view of an upper region of a drying apparatus according to another embodiment of the invention.

FIG. 30 is a front transparent view of an upper region of a drying apparatus according to another embodiment of the invention. For example, similar to the configuration shown in FIG. 9A, a connection between the flow generators 110 and the first air outlet 101 of the body 100 is such that the outlet of each of the flow generators 110 directly connects to the first air outlet 101 of the body 100. To provide added comfort for a user and/or increased drying efficiency, it may be desirable to further heat the air heated by the thermoelectric device 117. As seen in FIG. 30, air flowing from the filter unit 104 may pass by one side of the thermoelectric device 117 to be selectively heated or cooled.

While FIG. 30 shows a square shaped thermoelectric device 117 covering a portion of the outlet air flow pathway 105, it should be appreciated that the thermoelectric device 117 may be rectangular covering all of the outlet air flow pathway 105. That is, the thermoelectric device 117 may have a rectangular shape that covers all of the filtered air airflow pathway starting from the outlet of the filter unit 104 and ending at the inlet of the flow generator 110. Where the air is to be further heated, it may be desirable to heat the heated air downstream of the flow generator 110.

Thermal elements such as resistance heaters 120 may be provided at the downstream side of respective flow generators 110. The resistance heaters 120 may further heat the air forced by the flow generators 110 towards the first air outlet 101. The resistance heater 120 may be used as a booster to further heat or super heat the air heated by the thermoelectric device 117.

While in FIG. 30, the thermal elements are shown as resistance heaters, any other suitable thermal elements may be used. In other configurations the thermal element may be a thermoelectric device that may be used to selectively heat or cool the air at the downstream side of the flow generator.

Figure 31:
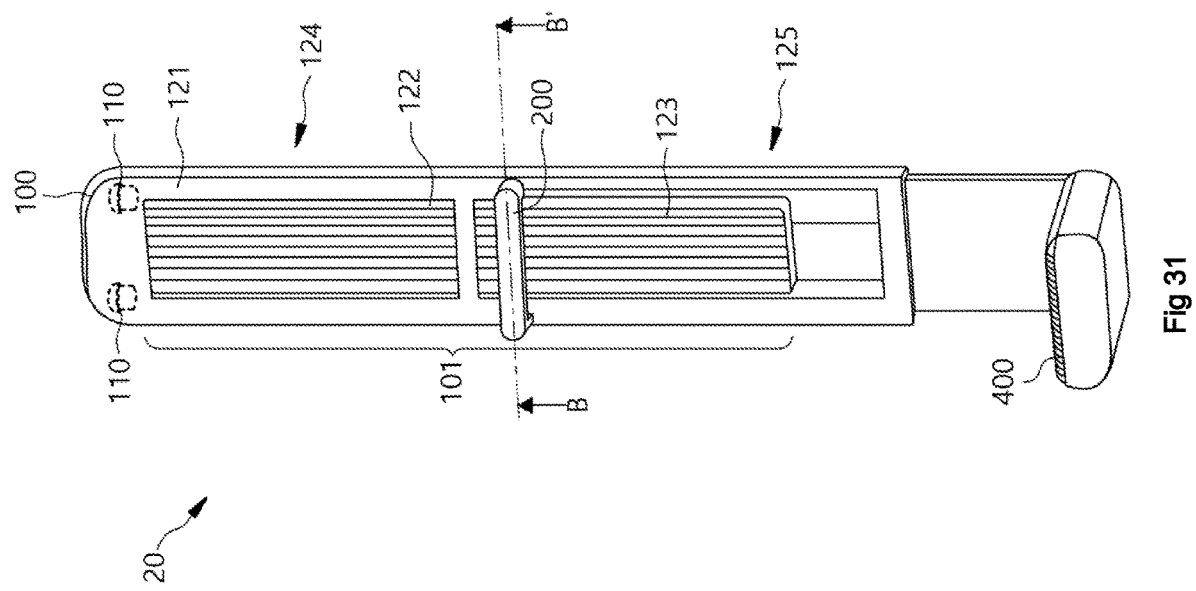
FIG. 31 is a perspective view of a drying apparatus according to an alternative embodiment of the present invention.
Figure 32:
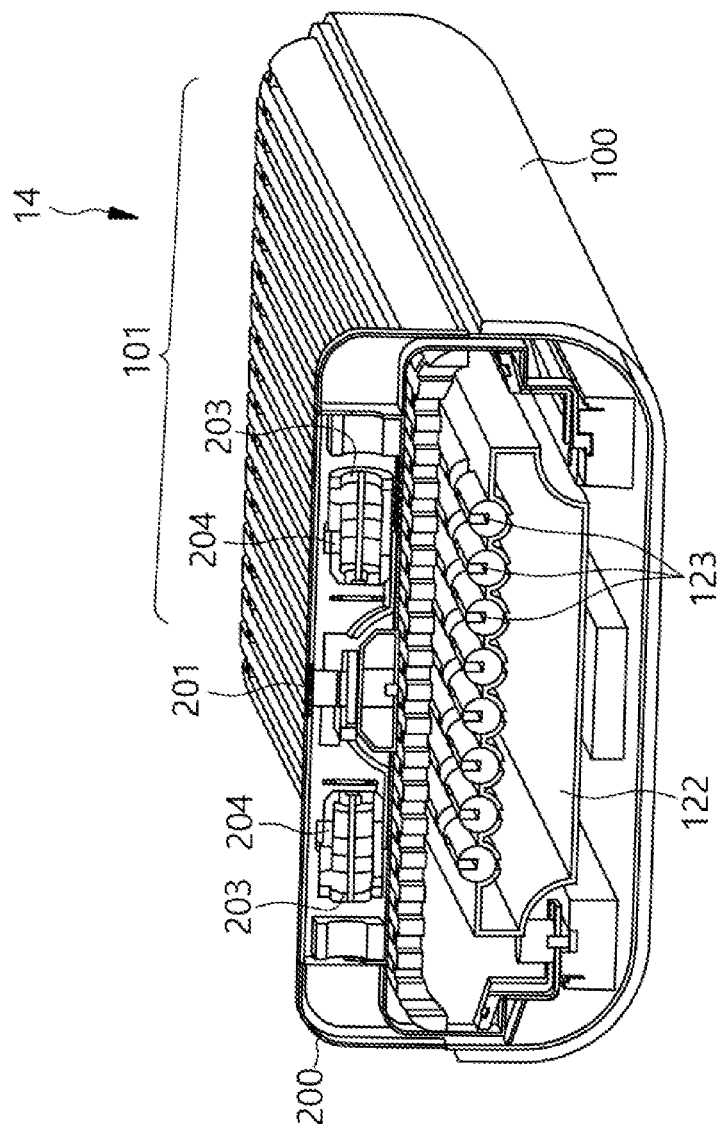
FIG. 32 shows a cross-sectional view along line B-B' of FIG. 31.

FIG. 31 illustrates a view of a drying apparatus 20 according to another exemplary embodiment of the present invention. FIG. 32 shows a cross-sectional view of a body 100 and a bar 200 of the drying apparatus of FIG. 31.

As shown in FIG. 31, in a drying apparatus 20, the first air outlet 101 may be distributed across at least a portion of the drying face of the body 100. Unlike the drying apparatus 10 described above, where the first air outlet 101 runs along a periphery of the body 100, the first air outlet 101 of the drying apparatus 20 includes outlet ducts 123 that are distributed across the face of the drying face 14. In the present embodiment, the outlet ducts 123 are a plurality of vertical slits running along a longitudinal length of the body 100 and disposed across the drying face 14. The outlet ducts 123 are provided in two zones, an upper zone 124 and a lower zone 129. This configuration may allow for differences in venting between different regions of the first air outlet 101.

FIG. 32 shows a cross-sectional view along line B-B' of FIG. 31 through the body 100 and the bar 200 where the first air outlet 101 is a distributed outlet across the drying face 14 of the body 100. In the drying apparatus 20, a pair of flow generators 110 may expel forced airflow to a duct 121 (similar to that shown in FIG. 8), to a duct 122, and finally on to a plurality of outlet ducts 123 from which the forced airflow is vented from the drying apparatus 20. Shown in cross-section is the duct 122 which may receive the forced airflow from the duct 121. The duct 122 may include a plurality of vertical slits running along a longitudinal length of the body 100 corresponding to the vertical slits of the outlet ducts 123. The duct 122 may vent the forced airflow to the plurality of outlet ducts 123 through the plurality of slits which, in turn is vented to the outside of the body 100 by the outlet ducts 123. The duct 122 and the plurality of outlet ducts 123 may comprise the first air outlet 101.

In this embodiment, the bar 200 may receive air from the flow generator or generators 110 of the body 100. For example, the bar 200 may have one or more air inlets, such as air inlets 203 as shown in FIG. 32. One example of a bar 200 having this configuration is shown in FIG. 16. Referring to FIG. 16, the bar 200 having a pair of air inlets 202 at the back side of the bar 200 may receive forced airflow from portions of the plurality of outlet ducts 123 which the pair of air outlets 202 covers. Referring to FIG. 32, the one or more air inlets 203 may receive air from the flow generators 110 in the body 100 and vent the air from the second air outlet 201.

In the present embodiment, the bar 200 is provided with a pair of flow generators 204 that further speeds the forced airflow received from the flow generators 110 of the body 100. However, in other embodiments, the bar 200 is not provided with flow generators 204 and vents the forced airflow received from the flow generators 110 of the body 100 as is. Although not shown, the bar 200 may include resistance heaters 120 as shown in FIG. 18. Although not shown, the bar 200 may include thermoelectric devices instead of resistance heaters. The bar 200 may further air condition the received forced airflow from the body 100. Otherwise, the bar 200 may not include an air conditioning device and may vent forced airflow air conditioned by the thermoelectric devices 117 of the body 100 without further air conditioning the received forced airflow from the body 100.

Referring back to FIG. 31, the drying apparatus 20 may further include a food pad 400 on which a person may place their feet. The duct 122 may continue on to connect to the foot pad 400. The duct 122 may supply air flow to one or more air outlets of the foot pad 400 through which air vented from the one or more air outlets may dry the feet of the person. In the configuration shown in FIG. 31, the foot pad 400 may be configured to retract into the body 100 of the drying apparatus 20, for example, when not in use. However, in other embodiments, the foot pad 400 does not retract and may be stationary supported by the floor. Further details of the drying apparatus including the foot pad will be described in detail below.

FIGS. 33A and 33B is a drying apparatus 10 that comprises a foot pad 400 according to an embodiment of the present invention. The foot pad 400 may be located at the lower portion of the drying apparatus 10. The drying apparatus 10 further includes a bar 200. Details of the bar 200 have been described above and will not be further described herein.

The foot pad 400 may assist the user in drying their lower limbs, and particularly their feet. As shown in FIG. 33A, the foot pad 400 may be stowed at the base of the drying apparatus 10. When a user desires to use the foot pad 400 (i.e. to stand on the upper surface of the foot pad) the user may deploy the foot pad 400 as shown in FIG. 33B. That is, the foot pad 400 orients from a stowed configuration in which the upper standing surface is aligned substantially vertical as shown in FIG. 33A to a deployed configuration where the upper standing surface is aligned substantially horizontal, ready for a user to stand on the upper surface of the foot pad 400.

The foot pad 400 may be rotatably connected to the body 100 through an extension 405. When not in use, the extension 405 may retract into the body 100 lifting the foot pad 400 with it. When in use, the extension 405 may protrude from the body 100 and lower the foot pad 400 from the body 100. FIG. 33B shows the foot pad 400 in use where the upper surface of the foot pad 400 is aligned substantially horizontal with respect to the body 100. When the use of the foot pad 400 is no longer needed, the extension 405 retracts lifting the foot pad 400. The foot pad 400 may be angled with respect to the body 100 as the foot pad 400 is being lifted, and subsequently, when the extension 405 is fully retracted into the body 100, the foot pad 400 may be aligned substantially vertical with respect to the body 100. This position of the foot pad 400 is shown in FIG. 33A. As shown in FIG. 33A, an end of the foot pad 400 may be closely in contact with a lower end of the body 100.

To make the drying apparatus 10 look pleasing, the contours of the foot pad 400 may follow the contours of the body 100 such that the foot pad 400 and the body 100 look like a single unit. That is, the contours of the body 100 may transition smoothly to the contours of the foot pad 400 where the end of the body 100 meets the end of the foot pad 400. Further, the other end of the foot pad 400 may take a form similar to if not identical to the other end of the body 100. Thus, the user viewing the drying apparatus 10 may think that the foot pad 400 is part of the body 100 of the drying apparatus 10. This is illustrated in FIG. 33A.

Alternatively, in one embodiment, the extension 405 is held on, or within, the body 100 of the drying apparatus 10. For example, the extension 405 may be held behind the molded plastic covering of the body 100 such that it is obscured when the foot pad 400 is in a stowed position. That is, the extension 405 is inserted into the body 100 such that, in the stowed position, the extension 405 is not visible from the outside.

The extension 405 may be protruded from the body 100 or be retracted to the body 100 using a drive apparatus similar to that shown in FIGS. 12A-12B. That is, instead of the drive apparatus moving the bar 200 up and down, the drive apparatus may move the extension 405 up and down. The extension 405 may be movably guided in the guide tracks at the body 100, that allow the extension 405 to slide vertically up and down. A drive assembly driving the extension 405 may include one or more motors that operate to raise and lower the extension 405. In certain configurations, the same drive apparatus 11 that moves the bar 200 up and down may also move the extension 405 up and down. In other configurations, the drive apparatus driving the extension 405 may be separate from the drive apparatus 11 driving the bar 200.

It should be noted that the drive apparatus driving the extension 405 is not limited to the configuration shown in FIGS. 12A-12B. For example, the drive apparatus driving the extension 405 may be a rack and pinion system. In another configuration, the extension 405 may be driven by a hydraulic system.

Figure 34:
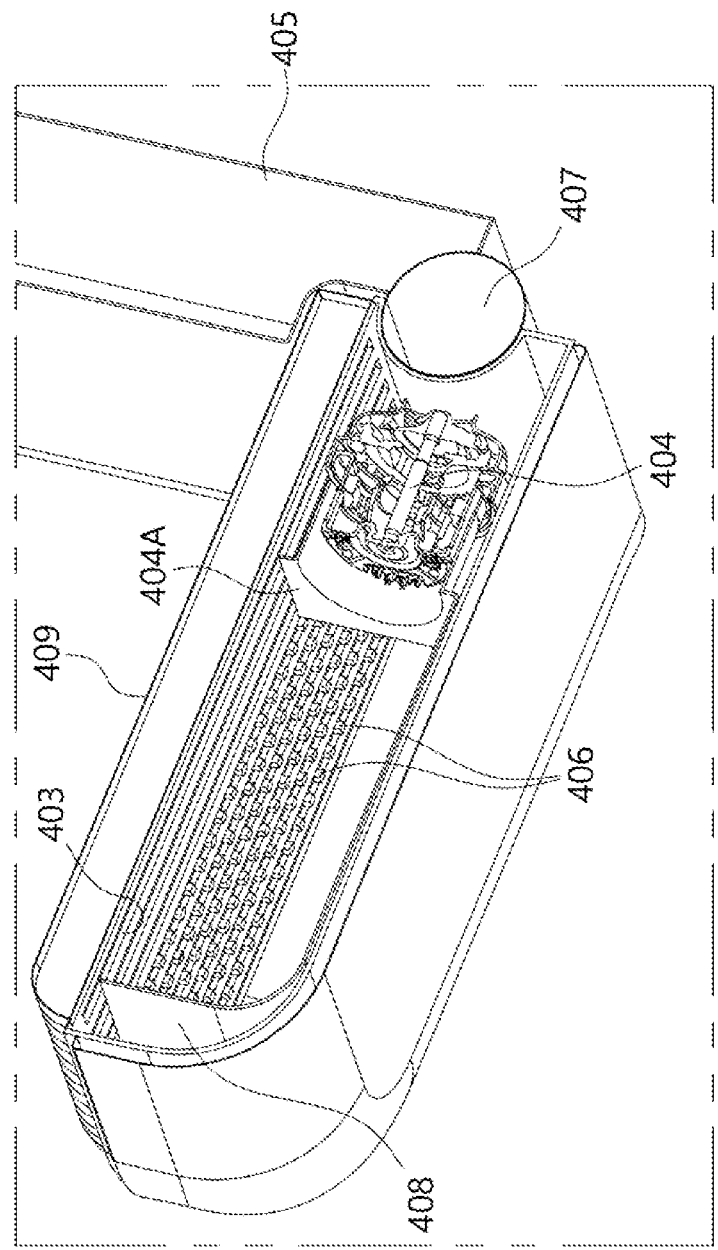
FIG. 34 is a partial view of various internal components of the foot pad.

FIG. 34 is a partial view of various internal components of the foot pad 400. There is shown in FIG. 34 a rotational connection 407 for the foot pad 400 to an extension 405. The rotational connection 407 allows the foot pad 400 to rotate about the horizontal axis between a vertical and horizontal condition. As shown in FIG. 34, the rotational connection 407 may comprise a shaft, or a tube, the foot pad 400 having a corresponding feature that mates to the shaft or tube, and allowing the foot pad 400 to rotate about the shaft or tube axis. Hence, the foot pad 400 may be rotatably connected to the extension 405. An operation of the rotational connection 407 is now described.

When in use, the extension 405 may protrude from the body 100 lowering the foot pad 400 with it. The upper surface of the foot pad 400 may be initially aligned substantially vertical with respect to the body 100. However, as the foot pad 400 makes contact with the ground below, the rotational connection 407 allows the foot pad 400 to pivot with respect to the ground. As the foot pad 400 is further lowered, the rotational connection 407 allows the foot pad 400 to be further angled with respect to the body 100. Finally, when the bottom surface of the foot pad 400 makes full contact with the ground, the foot pad 400 may be aligned substantially horizontally with respect to the body 100.

When the foot pad 400 is no longer used, the extension 405 may retract into the body 100 lifting the foot pad 400. The rotational connection 407 may allow the foot pad 400 to rotate about its axis such that the foot pad 400 may be angled with respect to the body 100 as the foot pad 400 is being lifted, and subsequently, when the extension 405 is fully retracted into the body 100, the foot pad 400 may be aligned substantially vertical with respect to the body 100.

As shown in FIG. 34, the drying apparatus 10 may include one or more ultraviolet (UV) light sources 406 such as UV light emitting diodes. Referring to the one or more UV light sources 406, for illustration purposes, the UV light emitting diodes (LEDs) will be used as an example. However, other UV light sources 406 may be used such as UV lamps. Using UV for disinfection is known as ultraviolet germicidal irradiation. UV may be classified as according to its wavelengths as UV-A (320-400 nm), UV-B (280-320 nm), and UV-C (100-280 nm). UV-A and UV-B are not particularly effective in killing germs. UV-C, on the other hand, may kill germs by destroying the nucleic acids and disrupting their DNA. In particular wavelengths of approximately 265 nm have shown to be very effective in killing germs. However, prolonged exposure to UV-C may cause sunburn and even skin cancer. Prolonged exposure may lead to vision impairment including damage to the eye retina. Another undesired effect of UV-C is that its exposure deteriorates plastic and rubber.

Another UV LED may be the blue LED operating at a wavelength of approximately 405 nm (violet), and approximately 460 nm (blue) which are known to kill germs. Blue light phototherapy results in absorption of blue light by the germ which subsequently causes membrane disruption. While not as effective as UV-C, 405 nm light is not as harmful to humans as UV-C or cause deterioration to plastics and rubber.

Figure 35A:
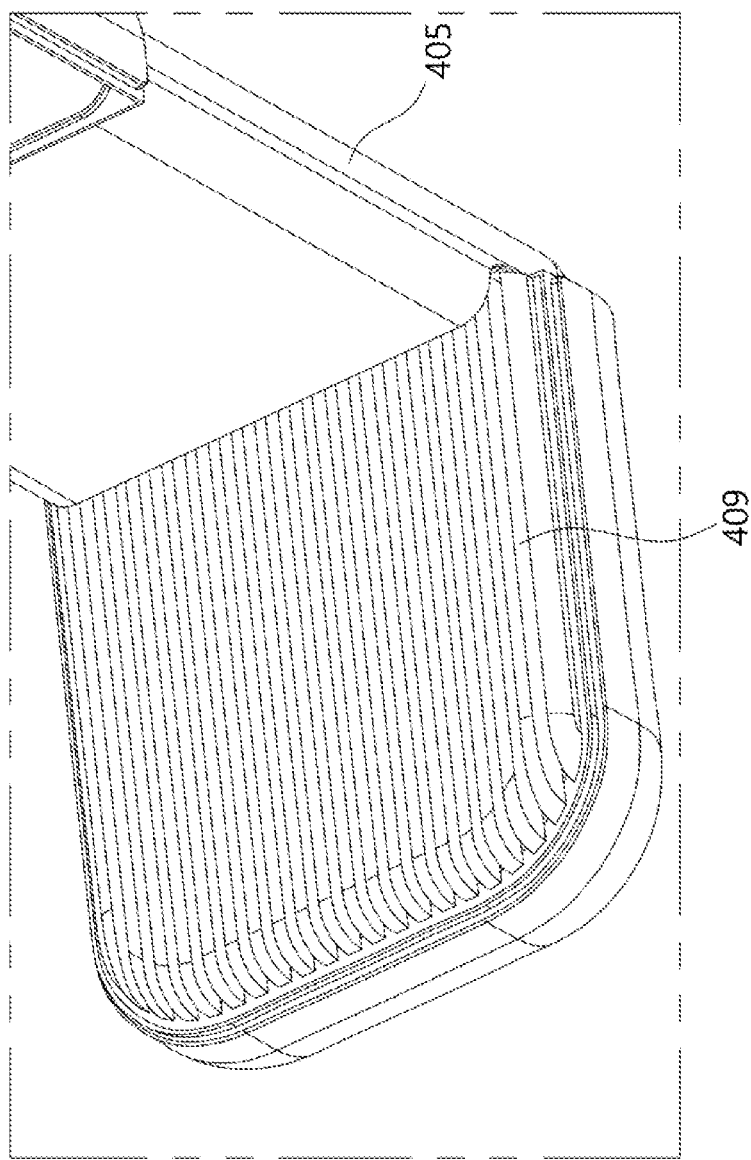
FIG. 35A is a view of the top surface of the foot pad.
Figure 35B:
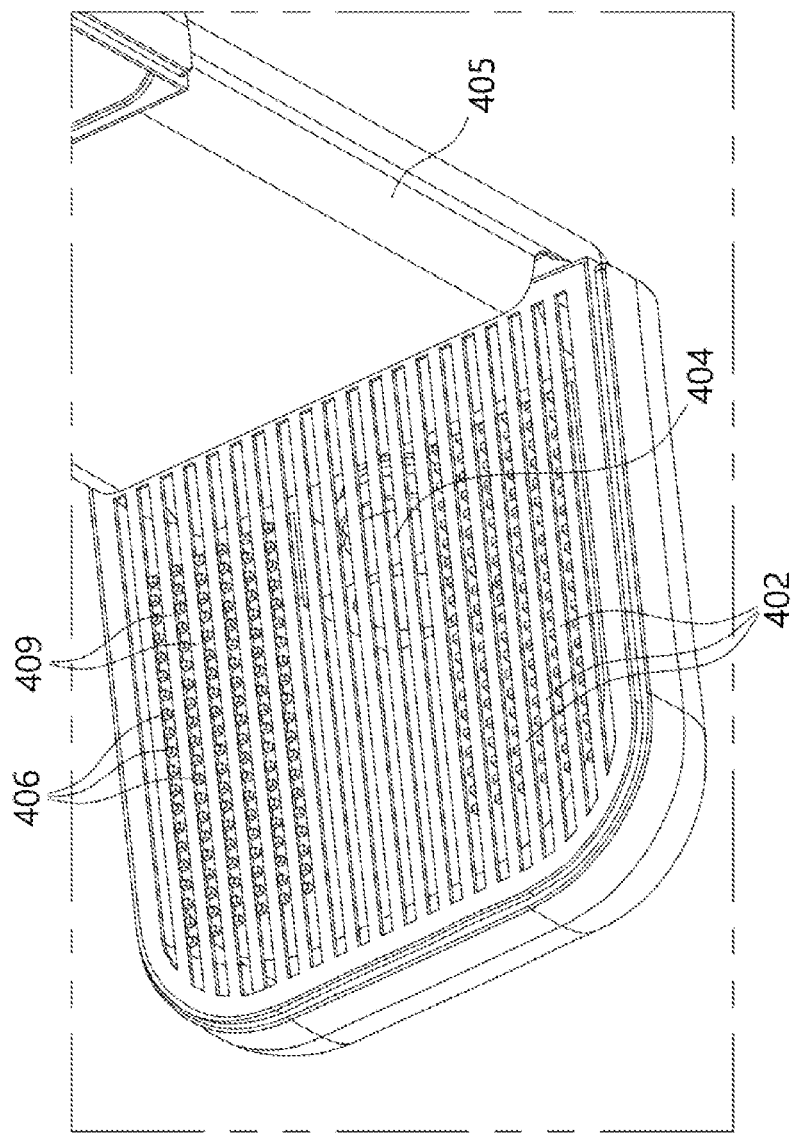
FIG. 35B is a top view of the foot pad showing various internal components of the foot pad.

The UV light source 406 may be formed as a matrix of UV LEDs arranged below a foot support 409 of the foot pad 400. The foot support 409 on which the user can place their feet is more clearly shown in FIG. 35A. FIG. 35B is a view in which the foot support 409 has been removed to show the UV light source 406 as a matrix of UV LEDs below the foot support 409. It should be noted that while FIGS. 34 and 35B show the UV LEDs as being arrayed under the top surface of the foot pad 400, the drying apparatus need not be limited to this configuration. For example, the UV LEDs may be located on the side, front or rear walls of the internal compartment of the foot pad 400. It will be appreciated that such an orientation is suitable provided the UV light can be used to disinfect the user's feet when they are placed on the foot support 409 of the foot pad 400.

Figure 36A:
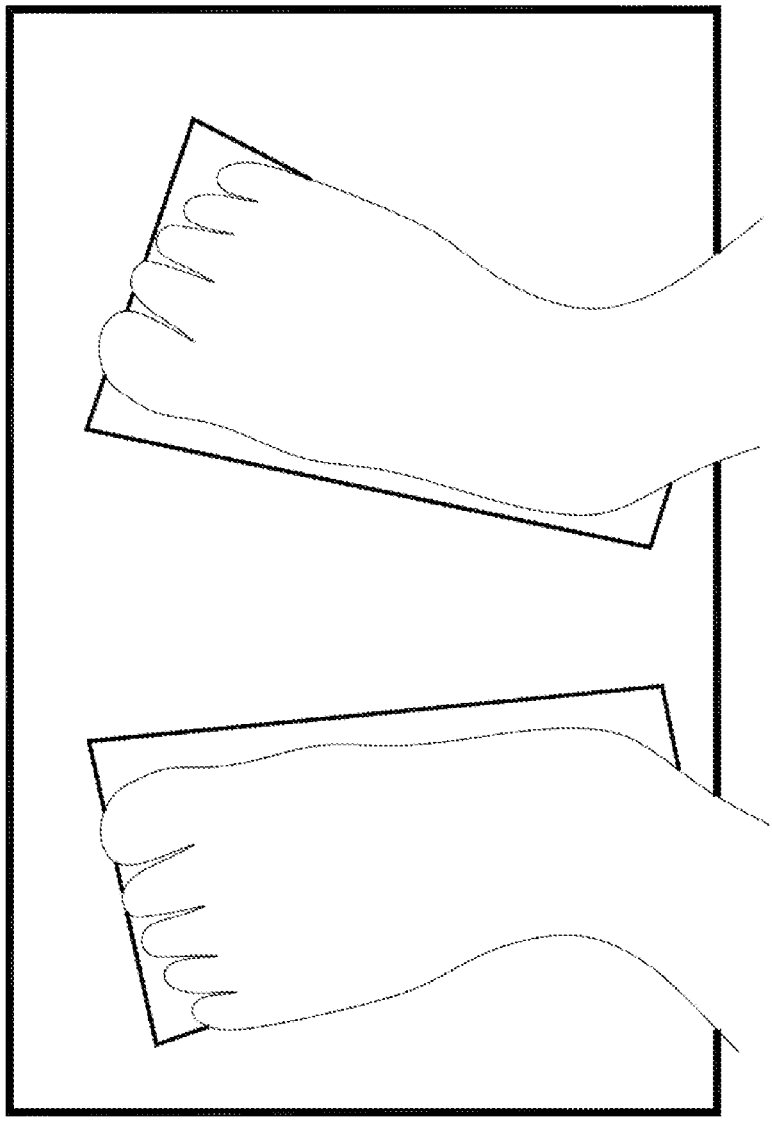
FIGS. 36A and 36B are stylized pictures of a user's feet showing their placement on the top surface of a foot pad (shown as a rectangular box) as either standing with their feet flat (FIG. 36A) or standing on their toes (FIG. 36B).

The UV light source may be located predominantly or solely below a zone on the foot pad where the user places their feet, as shown in FIG. 35B. For example, a user will typically stand on the foot support 409 with their feet slightly spread apart as shown in FIG. 36A. In one embodiment the top surface of the foot support 409 may have markings or indicia to indicate where the user is to place their feet. UV light may cause distraction and it may be that its exposure to the eyes may not be desirable. In another embodiment, the top surface of the foot support 409 may comprise a switch matrix using contact switches, or resistive or capacitive touchscreen similar to those found in smart phones or notepads, etc. When the user places their feet on the switch matrix of the foot support 409, a controller 53, for example, senses contacts or capacitance of the feet on the switch matrix and activates the UV light corresponding to the inner contours of the feet as shown in FIG. 36A while not activating the UV light outside of the feet.

The UV LEDs may also provide for disinfecting a surface of the first body 100 or a surface of the extension 405. That is, the UV LEDs may disinfect the vicinity of the drying apparatus 10.

In some embodiments the foot pad 400 receives air flow from the flow generator 110 of the body 100. In such an embodiment, the drying apparatus 10 includes a duct, such as the duct 122 shown in FIG. 32, from the flow generator 110 of the first body 100 to the airflow outlet 402 of the foot pad 400. In some embodiments, the bar 200 is movable to the lower portion of the body 100, and the bar 200 directs an air flow through the second air outlet 201 towards the foot pad 400.

In an alternate embodiment the foot pad 400 includes a foot pad flow generator 404. This is shown in FIG. 35B and more clearly shown in FIG. 34. The foot pad flow generator 404 may be an axial fan and the like. In one embodiment, the foot pad flow generator 404 may have a configuration similar to the flow generator 110, which has been described with respect to FIG. 9B. The foot pad flow generator 404 receives air from the foot pad airflow inlet 403 which is shown in FIG. 34. As shown in FIG. 34, the foot pad flow generator 404 may be located proximal to the attachment point of the foot pad 400 to the extension 405 or body 100 of the drying apparatus 10. The foot pad 400 may include a flow guide 408 that ducts air from the airflow inlet 403 of the foot pad 400 to the foot pad flow generator 404. The flow guide 408 may be spaced from the bottom surface of the foot pad 400 to create an airflow passage from the airflow inlet 403 of the foot pad 400 to the foot pad flow generator 404.

The airflow generator 404 may include a housing 404A that surrounds the airflow generator 404 with an outlet to direct the airflow to a desired direction. As described with respect to FIG. 9B, the housing 404A may increase the speed of airflow expelled from the foot pad flow generator 404 in one configuration.

Figure 36B:
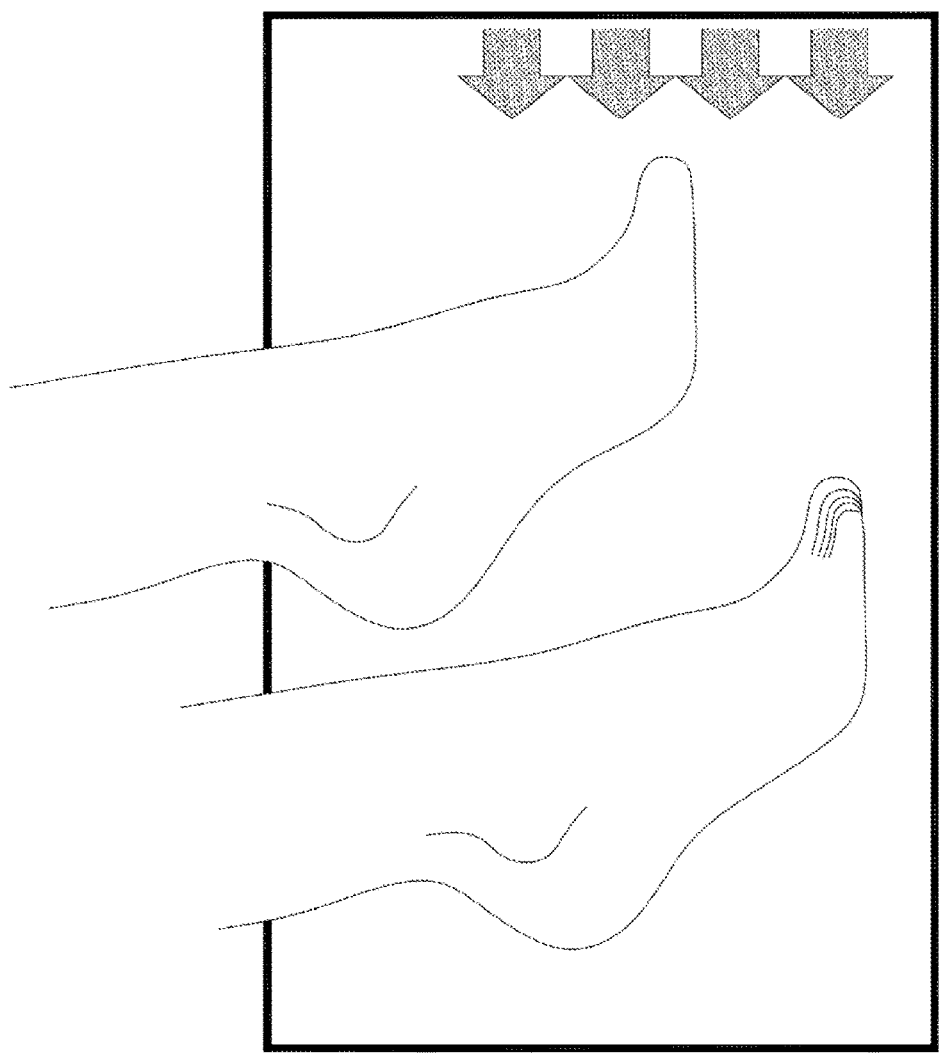

As shown in FIG. 34, the flow guide 408 may include a ramping portion whereby airflow directed from the foot pad flow generator 404 towards the ramping section is directed upwards through the foot pad airflow outlet 402. In one configuration, the airflow may be directed to a side of the foot pad such that the expelled air flows across the top surface of the foot pad, for example, as shown in FIG. 36B.

Referring to FIG. 35B, the foot pad airflow outlet 402 is located on the top surface of the foot pad 400 and provides for the airflow to contact the user's feet. As shown in FIG. 35B the foot pad airflow outlet 402 may comprise a plurality of slits. In one embodiment, the foot support 409 is not provided and the top surface of the foot pad 400 is made of sufficient strength to support the user and thereby functioning as a foot support. The slits extend the length and width of the top surface of the foot pad 400 allowing for airflow to outlet the surface area of the top surface of the foot pad to which the slits extend. In this embodiment, the switch matrix or the markings or indicia may be located on the top surface of the foot pad 400.

In some embodiments the foot pad 400 may comprise thermal elements such as resistance heaters provided at the downstream side of the foot pad flow generator 404. The resistance heaters may heat the air forced by the foot pad flow generators 404 towards the foot pad airflow output 402.

As described above with reference to FIG. 35A, the foot pad 400 may include a foot support 409 that covers substantially the top surface of the foot pad 400. The foot support 409 may have slits that align with the slits of the foot pad airflow outlet 402. The foot support 409 may provide for a more comfortable surface for the user to stand on. Additionally, the foot support may be replaceable, so that it can be easily replaced as it wears.

Referring now to FIGS. 36A and 36B, when in use, the user can place their feet flat on the surface of the foot pad 400 (FIG. 36A) or stand on their toes (FIG. 36B). In the configuration shown in FIG. 36A, the footpad airflow outlet 402 may be on the top surface of the foot pad 400. By placing their feet flat on the surface of the foot pad 400, the user may dry their feet. In the configuration shown in FIG. 36B, the foot pad airflow outlet may be at a side of the foot pad 400, and when the user places their feet with only their toes on the top surface of the foot pad 400, standing on their toes may enhance the drying effect on their feet.

In some embodiments the drying apparatus 10 provides vertical, horizontal and/or angled air flow over the top surface of the foot pad 400. Such air flow may come from the first air outlet 101 and/or the second air outlet 201.

Figure 38:
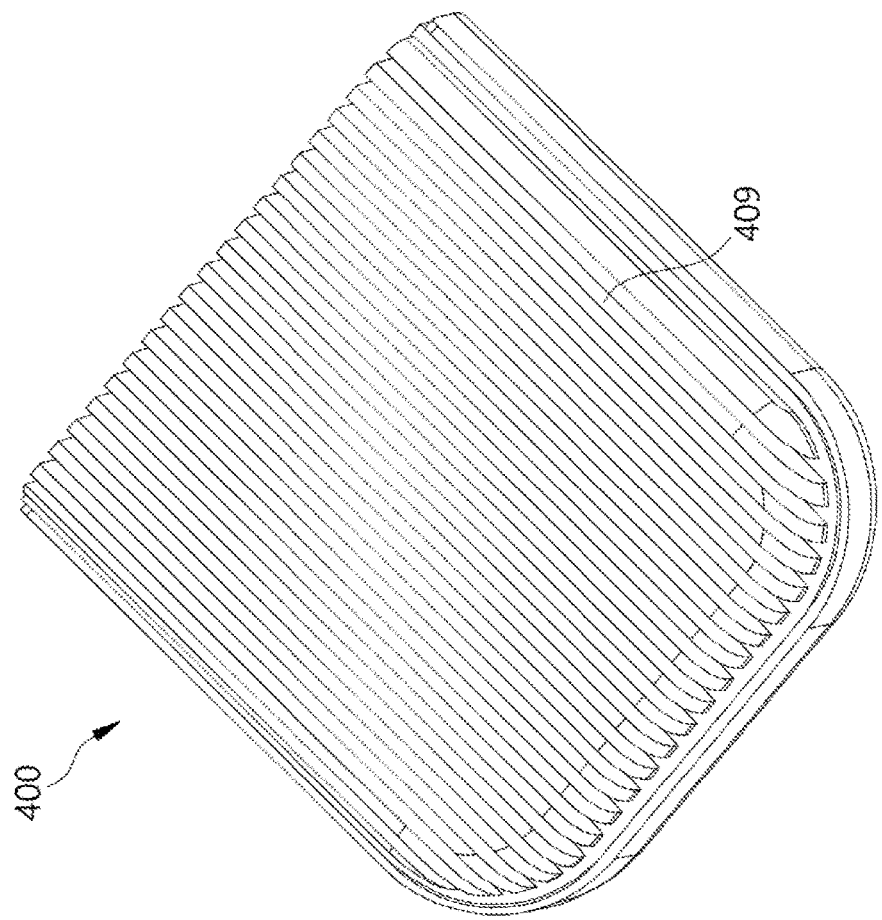
FIG. 38 is a top perspective view of the top surface of a detached foot pad.

FIGS. 37 and 38 show another embodiment in which the foot pad is detachable from the drying apparatus. For example, the foot pad 400 may be used in conjunction with the extension 405 as described above and/or used separately from the drying apparatus 10.

It will be appreciated that when used in a detachable configuration, the foot pad 400 includes a foot pad flow generator 404 separate to any flow generator provided on the drying apparatus 10.

In those embodiments providing a detachable foot pad 400, the foot pad may include a power source 410. For example, the foot pad 400 may include a rechargeable battery that drives the foot pad flow generator 404 when it is disconnected from the body 100 of the drying apparatus 10. Once the user finishes drying their feet using the foot pad 400, the foot pad 400 may be reattached to the body 100 of the drying apparatus 10. In some embodiments when the foot pad 400 is reattached to the body 100 of the drying apparatus 10, the drying apparatus 10 comprises a complementary electrical connection that charges the rechargeable battery of the foot pad 400.

Figure 39:
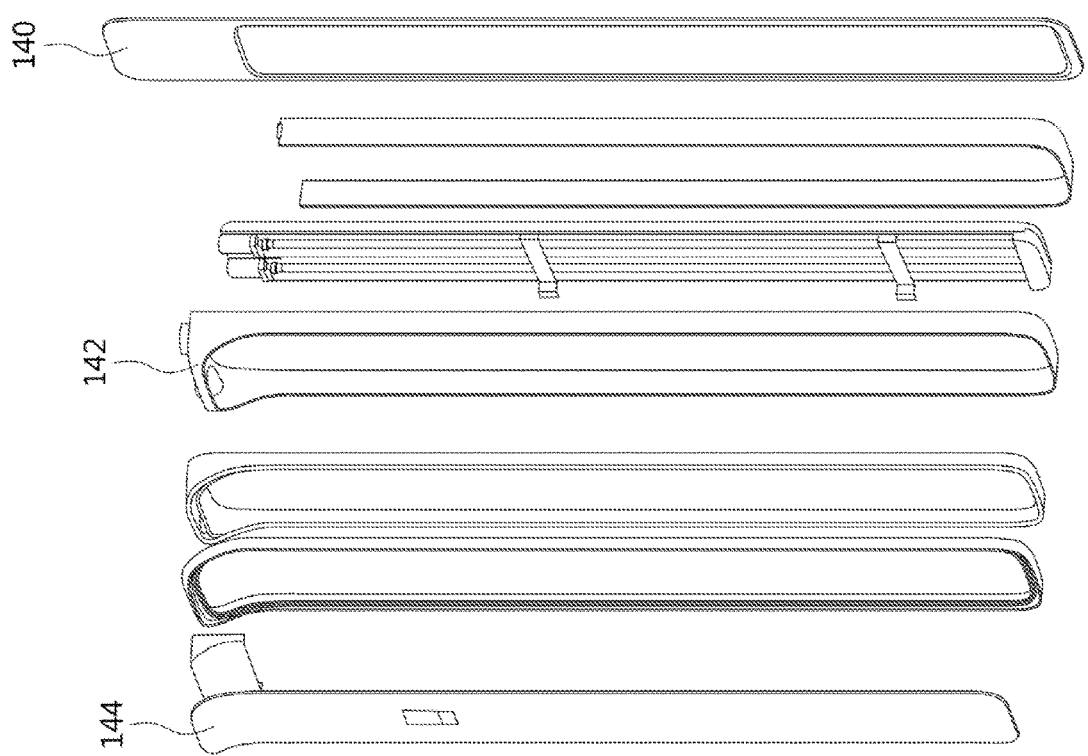
FIG. 39 is an exploded view of components of a drying apparatus according to an embodiment of the present invention.

FIG. 39 is an exploded view of the body according to an embodiment of the present.

The body 100 may be covered with molded plastic covering. As shown in FIG. 39, the molded plastic covering may comprise a back panel 140, a side panel 142 and a front panel 144 covering the body 100. In another embodiment, the plastic covering may have a thin metallic plate adhered to its surface. Parts of the plastic covering may be snap fitted together. For example, one part may have a protrusion portion and another part to be fitted to may have a corresponding recess portion. When the two parts are snap fitted together, the protrusion portion fits into the recess portion and the two parts are fixed to each other. The plastic covering form an outer appearance of the body 100 and provide an aesthetically pleasing look. Being snap fitted together, the plastic covering of the body 100 may be removed by pulling the plastic covering off the body 100 and replacing with another plastic covering having a design or pattern meeting the preference of the user, and thereby being customized to the user according to their taste. It should be noted that the plastic covering 230 (see FIG. 18) of the bar 200 may also be removed and replaced with another plastic covering having a design or pattern meeting the preference of the user, and thereby being customized to the user according to their taste.

Exemplary embodiments of the drying apparatus have been described above. Embodiments may be modified for particular usage or suitability.

Where in the foregoing description reference has been made to elements or integers having known equivalents, then such equivalents are included as if they were individually set forth.

Although embodiments have been described with reference to a number of illustrative embodiments thereof, it will be understood by those skilled in the art that various changes in form and details may be made therein without departing from the spirit and scope of the invention as defined by the appended claims. Therefore, the preferred embodiments should be considered in a descriptive sense only and not for purposes of limitation, and also the technical scope of the invention is not limited to the embodiments. Furthermore, the present invention is defined not by the detailed description of the invention but by the appended claims, and all differences within the scope will be construed as being comprised in the present disclosure.

None of the features recited herein should be interpreted as invoking 35 U.S.C. § 112(f) unless the term "means" is explicitly used.

Many modifications will be apparent to those skilled in the art without departing from the scope of the present invention as herein described with reference to the accompanying drawings.

What is claimed is:

1. A drying apparatus comprising:
   a body;
   a bar movable relative to the body;
   an air inlet;
   a flow generator to receive inlet air from the air inlet and generate an airflow;

a second airflow outlet at the bar; and a foot pad having a top surface and a bottom surface attachable to a lower portion of the body, the foot pad comprising a foot pad airflow outlet.

2. The drying apparatus of claim 1, wherein the flow generator is disposed in the body and the foot pad airflow outlet is in fluid communication with the flow generator.

3. The drying apparatus of claim 1 wherein the top surface of the foot pad is a standing surface having one or more foot pad airflow outlets, wherein in use the standing surface is adapted for placement of a user's feet.

4. The drying apparatus of claim 1, wherein the foot pad airflow outlet is disposed at a side of the foot pad.

5. The drying apparatus of claim 1, wherein the foot pad comprises a flow generator in fluid communication with the foot pad airflow outlet.

6. The drying apparatus of claim 3, wherein the standing surface comprises a plurality of slots, the slots providing for the one or more foot pad airflow outlets.

7. The drying apparatus of claim 6 wherein the slots extend substantially a width of the standing surface of the foot pad.

8. The drying apparatus of claim 1, wherein the foot pad comprises an ultraviolet (UV) light source disposed at the foot pad.

9. The drying apparatus of claim 8, wherein the UV light source includes wavelengths in a range from 100 nm to 280 nm, 405 nm, or 460 nm.

10. The drying apparatus of claim 8, wherein the top surface comprises a switch matrix and the UV light source comprises a plurality of UV light emitting diodes (LEDs), wherein the plurality of UV LEDs are selectively activated based on an activation at the switch matrix corresponding to a user's feet.

11. The drying apparatus of claim 1, having a stowed condition in which the foot pad is connected to the body and the top surface is vertically aligned, and a deployed condition in which the foot pad is moved relative to the body and the top surface is substantially horizontally aligned.

12. The drying apparatus of claim 1, wherein the foot pad is connected to an extension, the extension held on, or within, the body, the extension vertically moveable relative to the body.

13. The drying apparatus of claim 1, wherein the foot pad is rotationally connected to the body or the extension, wherein the attachment allows for at least 90 ☐ rotation of the foot pad relative to the body.

14. The drying apparatus of claim 1, comprising and a motor operable to rotate the foot pad along a horizontal axis with respect to the body, a controller configured to control the motor to adjust an orientation of the foot pad.

15. The drying apparatus of claim 14, wherein the drying apparatus has a stowed condition in which the foot pad is connected to the body and the top surface is vertically aligned, and a deployed condition in which the foot pad is moved relative to the body and the top surface is horizontally aligned, and the controller is configured to move the foot pad between the stowed condition and the deployed condition.

16. The drying apparatus of claim 1, wherein the bar is moveable to the lower portion of the body, and the bar is adapted to direct a flow of air towards the user's feet.

17. The drying apparatus of claim 16, further comprising a bar flow generator located at the bar, the bar flow generator generating the flow of the air at the bar.

18. The drying apparatus of claim 12, wherein the foot pad is detachable from the body or the extension.

19. The drying apparatus of claim 5, wherein the foot pad flow generator is disposed in the foot pad proximal to the body or extension, and the air flow inlet is located distally from the body or extension.

20. The drying apparatus of claim 19 wherein the foot pad comprises an airflow inlet at the distal end of the foot pad, and a flow guide disposed below the flow generator, wherein the flow guide is spaced from the bottom surface of the foot pad to define a flow passage from the air inlet to the flow generator.

* * * * *